(12) United States Patent
Sylliaasen et al.

(10) Patent No.: US 11,504,178 B2
(45) Date of Patent: Nov. 22, 2022

(54) EXHAUST COLLECTION BAG FOR CRYOGENIC TREATMENT

(71) Applicant: Channel Medsystems, Inc., Emeryville, CA (US)

(72) Inventors: Scott Sylliaasen, San Francisco, CA (US); Ric Cote, Oakland, CA (US); William Malecki, Piedmont, CA (US)

(73) Assignee: Channel Medsystems, Inc., Berkeley, CA (US)

( * ) Notice: Subject to any disclaimer, the term of this patent is extended or adjusted under 35 U.S.C. 154(b) by 338 days.

(21) Appl. No.: 15/288,766

(22) Filed: Oct. 7, 2016

(65) Prior Publication Data

US 2017/0112559 A1 Apr. 27, 2017

Related U.S. Application Data

(60) Provisional application No. 62/239,139, filed on Oct. 8, 2015.

(51) Int. Cl.
| | |
|---|---|
| *A61B 18/02* | (2006.01) |
| *A61J 1/14* | (2006.01) |
| *A61J 1/10* | (2006.01) |
| *A61M 27/00* | (2006.01) |
| *A61B 18/00* | (2006.01) |

(52) U.S. Cl.
CPC .......... *A61B 18/02* (2013.01); *A61J 1/10* (2013.01); *A61J 1/1475* (2013.01); *A61J 1/1493* (2013.01); *A61M 27/00* (2013.01); *A61B 2018/0022* (2013.01); *A61B 2018/00041* (2013.01); *A61B 2018/00559* (2013.01); *A61B 2018/00577* (2013.01); *A61B 2018/025* (2013.01)

(58) Field of Classification Search
CPC .......... A61B 18/02; A61B 2018/00041; A61B 2018/0022; A61B 2018/00559; A61B 2018/00577; A61B 2018/025; A61J 1/10; A61J 1/14; A61J 1/1462; A61J 1/1475; A61J 1/1468
See application file for complete search history.

(56) References Cited

U.S. PATENT DOCUMENTS

| | | | |
|---|---|---|---|
| 4,578,074 | A | 3/1986 | Van Leerdam et al. |
| 5,405,333 | A | 4/1995 | Richmond |
| 6,159,160 | A | 12/2000 | Hsei et al. |
| 6,270,476 | B1 | 8/2001 | Santoianni et al. |

(Continued)

FOREIGN PATENT DOCUMENTS

| | | |
|---|---|---|
| CN | 2170109 | 6/1994 |
| CN | 2232762 | 8/1996 |

(Continued)

*Primary Examiner* — Kai H Weng
(74) *Attorney, Agent, or Firm* — Levine Bagade Han LLP

(57) ABSTRACT

An exhaust collection bag for cryogenic treatment is described herein and may generally comprise a first layer and a second layer attached along a periphery and forming an enclosed volume. The periphery defines four radiused corners and an extension member. A tubing connector may be positioned along the first layer and extend through the first layer and may also be located along a centerline of the first layer and in proximity to a bottom edge of the first layer. A drain closure may also be positioned along the first layer and located away from the centerline and in proximity to the bottom edge.

25 Claims, 20 Drawing Sheets

(56) References Cited

U.S. PATENT DOCUMENTS

| | | |
|---|---|---|
| 6,270,493 B1 | 8/2001 | Lalonde et al. |
| 6,280,439 B1 | 8/2001 | Martin et al. |
| 6,283,959 B1 | 9/2001 | Lalonde et al. |
| 6,471,680 B1 * | 10/2002 | Cawood ............... A61F 5/4405 604/327 |
| 6,554,780 B1 | 4/2003 | Sampson et al. |
| 6,569,158 B1 | 5/2003 | Abboud et al. |
| 6,743,184 B2 | 6/2004 | Sampson et al. |
| 6,872,183 B2 | 3/2005 | Sampson et al. |
| 7,063,670 B2 | 6/2006 | Sampson et al. |
| 7,101,367 B2 | 9/2006 | Xiao et al. |
| 7,381,208 B2 | 6/2008 | van der Walt et al. |
| 7,500,973 B2 | 3/2009 | Vancelette et al. |
| 8,206,345 B2 | 6/2012 | Abboud et al. |
| 8,225,643 B2 | 7/2012 | Abboud et al. |
| 8,343,129 B2 | 1/2013 | Falkvall et al. |
| 8,382,747 B2 | 2/2013 | Abboud et al. |
| 9,027,389 B2 | 5/2015 | Abboud et al. |
| 2002/0056725 A1 | 5/2002 | Wilcox et al. |
| 2005/0059952 A1 | 3/2005 | Giuliano et al. |
| 2006/0189962 A1 * | 8/2006 | Burtoft ............... A61F 5/4405 604/544 |
| 2008/0172016 A1 * | 7/2008 | House ............... A61F 5/44 604/317 |
| 2009/0030396 A1 | 1/2009 | Ferris |
| 2009/0030398 A1 | 1/2009 | Yodfat et al. |
| 2011/0062703 A1 * | 3/2011 | Lopez ............... A61M 39/22 285/129.1 |
| 2015/0289920 A1 | 10/2015 | Burnett et al. |

FOREIGN PATENT DOCUMENTS

| | | |
|---|---|---|
| CN | 1498183 | 5/2004 |
| CN | 1227142 | 11/2005 |
| CN | 101090666 | 12/2007 |
| CN | 203710364 | 7/2014 |
| EP | 1883386 | 2/2008 |
| WO | WO 1997/014493 | 4/1997 |
| WO | WO 2006/130378 | 12/2006 |
| WO | WO 2014/126473 | 8/2014 |
| WO | WO 2017/062747 | 4/2017 |

* cited by examiner

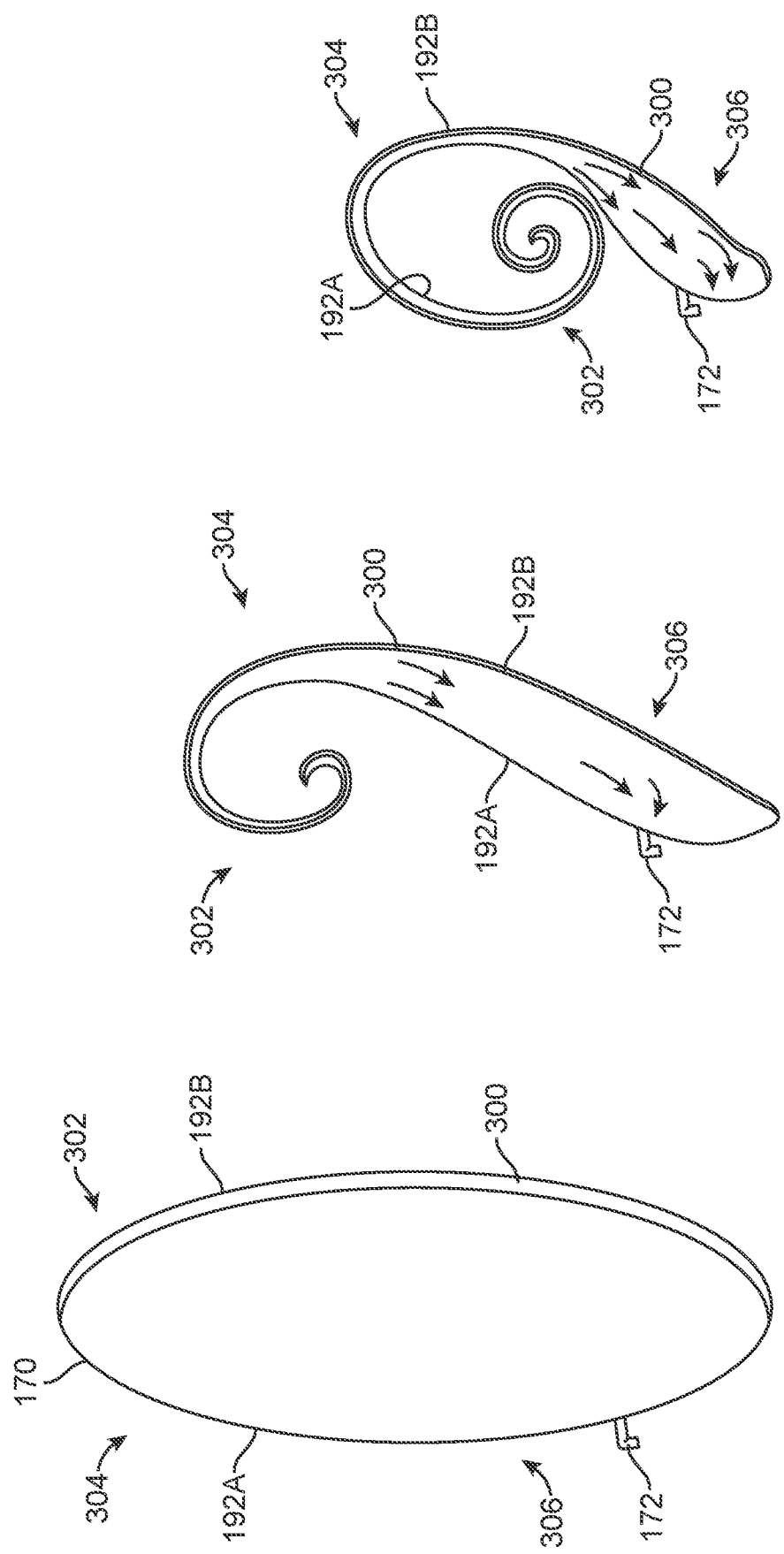

EXHAUST COLLECTION BAG FOR CRYOGENIC TREATMENT

CROSS-REFERENCE TO RELATED APPLICATIONS

This application claims the benefit of priority to U.S. Provisional Application No. 62/239,139 filed Oct. 8, 2015, which is incorporated herein by reference in its entirety.

FIELD OF THE INVENTION

The present invention relates to medical devices. In particular, the present invention relates to methods and apparatus for collecting exhaust gases generated from the cryoablative treatment of tissue regions.

BACKGROUND OF THE INVENTION

In the last few decades, therapeutic intervention within a body cavity or lumen has developed rapidly with respect to delivery of energy via radiofrequency ablation. While successful in several arenas, radiofrequency ablation has several, major downsides, including incomplete ablation, frequent lack of visualization during catheter insertion, potential for overlap during treatment (with some areas receiving twice as much energy as other areas), charring of tissues and requirements for frequent debridement, frequent requirements for additional doses of energy after debridement, and potential perforation of the body cavity or lumen due to the rigidity of the RF electrodes.

The current state of the art would benefit from minimally invasive devices and methods which deliver thermal energy to a desired area or extract energy from a desired area, in a consistent, controlled manner that does not char or inadvertently freeze certain tissues or create excessive risk of unwanted organ or lumen damage.

SUMMARY OF THE INVENTION

Generally, devices for delivering controlled treatment may comprise an elongate probe having a distal tip and a flexible length, at least one infusion lumen positioned through or along the elongate probe, wherein the infusion lumen defines one or more openings along its length, a liner expandably enclosing the probe, an inflow reservoir or canister valve fluidly coupled with a reservoir or canister containing a cryoablative agent, a modulation control unit fluid coupled with the inflow reservoir or canister valve and in fluid communication with the at least one infusion lumen, and a warming element thermally coupled with the reservoir or canister.

One method for utilizing the treatment assembly for cryoablatively treating tissue, e.g., uterine tissue, may generally comprising monitoring a temperature or pressure of the reservoir or canister containing a cryoablative agent, maintaining the temperature of the reservoir or canister at a predetermined level, positioning an elongate probe into a body lumen to be treated, expanding a liner enclosing the probe into contact against the body lumen, and infusing a cryoablative agent through a delivery lumen such that the cryoablative agent passes into an infusion lumen, through one or more unobstructed openings, and into contact against an interior of the liner.

In controlling or modulating the flow of the cryoablative agent, the inflow reservoir or canister valve which is fluidly coupled with the reservoir or canister may be utilized. Such a valve may generally comprising a valve body, a reservoir interface extending from the valve body and configured for fluidly coupling with the reservoir or canister containing the cryoablative agent, a modulation control interface defined along the body and configured for fluidly coupling to a modulation control interface, a valve stem seated within a valve stem channel defined within the valve body, an inflow lumen defined through the valve body and extending between the reservoir interface and the modulation control interface, where the valve stem is movable between a first position which obstructs the inflow lumen and a second position which opens the inflow lumen, a venting lumen defined through the valve body and extending between the reservoir interface and a vent opening, and a vent piston which is movable between a first position which obstructs the venting lumen and a second position which opens the venting lumen. Alternatively, the valve stem may be configured to include three positions including a first position which obstructs the inflow lumen, a second position which opens the inflow lumen, and a third optional position which opens the venting lumen.

To facilitate the liner expanding and conforming readily against the tissue walls of the uterus, the liner may be inflated with a gas or liquid. Once the elongate shaft has been introduced through the cervix and into the uterus, the distal opening of the shaft may be positioned distal to the internal os and the liner may be deployed either from within the shaft or from an external sheath. The liner may be deployed and allowed to unfurl or unwrap within the uterus. The cooling probe may be introduced through the shaft and into the liner interior. As the cryoablative agent (e.g., cryoablative fluid) is introduced into and distributed throughout the liner interior, the exhaust catheter may also define one or more openings to allow for the cryoablative fluid to vent or exhaust from the interior of the liner.

A coolant reservoir, e.g., nitrous oxide canister, may be fluidly coupled to the handle and/or elongate shaft via a coolant valve which may be optionally controlled by the microcontroller. The coolant reservoir may be in fluid communication with the cooling probe assembly and with the interior of the balloon. Additionally, an exhaust lumen in communication with the elongate probe and having a back pressure valve may also include a pressure sensor where one or both of the back pressure sensor and/or valve may also be in communication with the microcontroller.

The reservoir or canister may be inserted into the reservoir housing and into secure engagement with a reservoir or canister valve which may be coupled to the reservoir engagement control. The valve may be adjusted to open the reservoir or canister for treatment or for venting of the discharged cryoablative fluid during or after treatment. An inflow modulation control unit (e.g., an actuatable solenoid mechanism) may be coupled directly to the reservoir or canister valve and the cryoablative fluid line may be coupled directly to the modulation control unit and through the sheath and into fluid communication within the liner.

With the discharged cryoablative fluid in a completely gaseous state, the evacuating exhaust line may be vented to the surrounding environment or optionally coupled to a scavenging system to collect the discharged gas to limit exposure. Such scavenging collection systems may incorporate features such as orifices or valves to prevent any vacuum applied by the scavenging unit from interfering with the backpressure within the treatment device.

In one variation, an exhaust collection bag may be supported by a pole and connected to the exhaust line for collecting the exhaust fluids or gases. The evacuating exhaust line may be removably coupled to the collection bag via a tubing connector located near or at a bottom of the collection bag. The bag itself may be formed from two layers of a lubricious materials which are attached or welded (e.g., RF dielectric welded) around its periphery along its edges. Moreover, the collection bag may be configured to form an extension which projects from the bag and forms an opening for passing a hook through or to provide a point for attachment. The collection bag may be designed to hang, e.g., from an IV pole as shown such that it is maintained off the floor to keep it clean should a user want to reuse it a number of times.

The bag may be fabricated from, e.g., a polyurethane film, selected for its lubricity, elasticity, clarity, low cost and ability to be RF dielectric welded. The film may have a thickness of, e.g., 0.003 inches. Because the bag inflates at relatively low pressures, the lubricity of the layers prevents the layers of film from sticking together and allows the bag to readily inflate. Also, to accommodate potential volume increases associated with increased temperatures, the bag material also exhibits elasticity, e.g., film elongation may be on the order of 800%. The bag may be fabricated to have a burst pressure of at least greater than or equal to, e.g., ≥3 psi. The bag may also be fabricated so as to be at least partially transparent so that the clarity of the bag results in an object that visually occupies less space in the procedure room because objects can be seen through it.

The tubing connector may further incorporate one or more variations of a support member which may function as a tenting structure to prevent the layers of the bag from collapsing upon itself and trapping any exhaust gases. Additionally and/or optionally, the bag itself may incorporate features which enable the bag to collapse upon itself to force exhaust gases out of the bag interior.

BRIEF DESCRIPTION OF THE DRAWINGS

FIGS. 20A to 20C show side views of a bag incorporating a self-coiling support member which may extend along the length of the bag.

DETAILED DESCRIPTION OF THE INVENTION

Figure 1A:
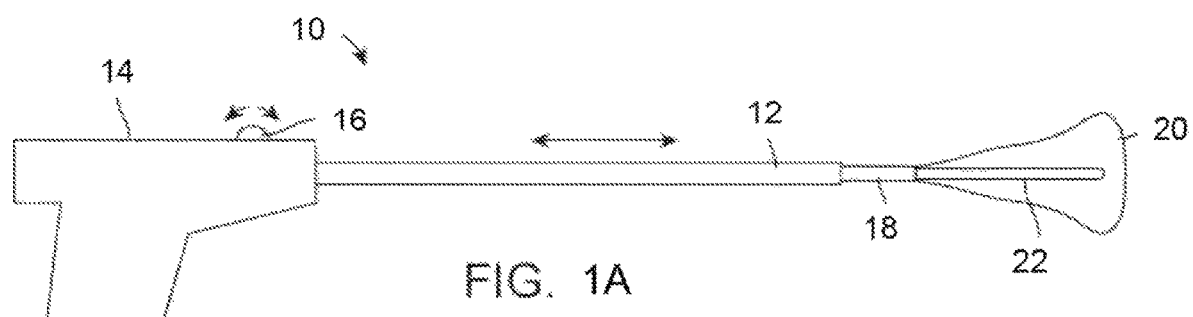
FIG. 1A shows a side view of an integrated treatment assembly.

The cooling probe 22 as well as the balloon assembly may be variously configured, for instance, in an integrated treatment assembly 10 as shown in the side view of FIG. 1A. In this variation, the assembly 10 may integrate the elongate shaft 18 having the liner or balloon 20 extending therefrom with the cooling probe 22 positioned translatably within the shaft 18 and liner 20. A separate translatable sheath 12 may be positioned over the elongate shaft 18 and both the elongate shaft 18 and sheath 12 may be attached to a handle assembly 14. The handle assembly 14 may further comprise an actuator 16 for controlling a translation of the sheath 12 for liner 20 delivery and deployment.

Figure 1B:
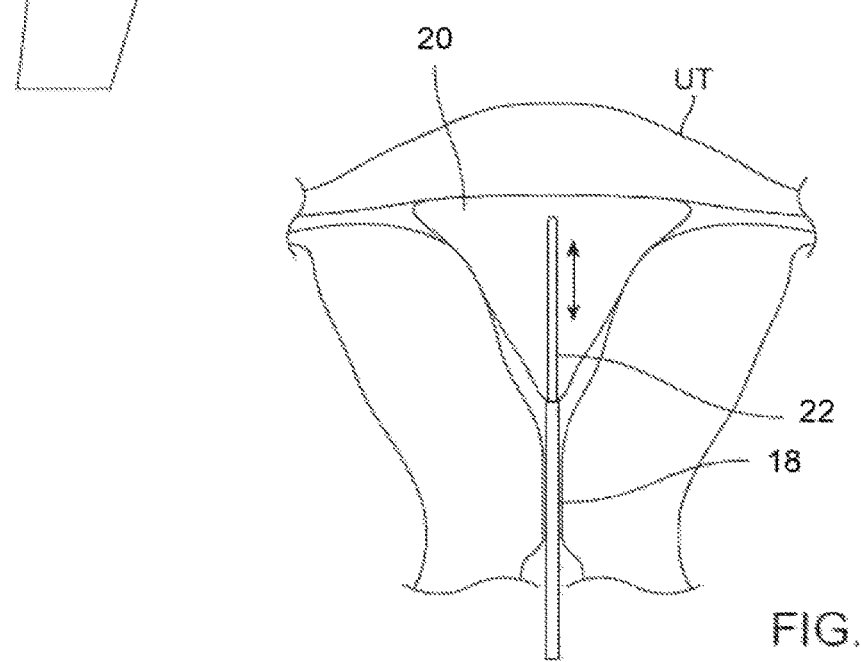
FIG. 1B shows an example of the assembly advanced through the cervix and into the uterus where the sheath may be retracted via the handle assembly to deploy the balloon.

With the sheath 12 positioned over the elongate shaft 18 and liner 20, the assembly 10 may be advanced through the cervix and into the uterus UT where the sheath 12 may be retracted via the handle assembly 14 to deploy the liner 20, as shown in FIG. 1B. As described above, once the liner 20 is initially deployed from the sheath 12, it may be expanded by an initial burst of a gas, e.g., air, carbon dioxide, etc., or by the cryoablative fluid. In particular, the tapered portions of the liner 20 may be expanded to ensure contact with the uterine cornu. The handle assembly 14 may also be used to actuate and control a longitudinal position of the cooling probe 22 relative to the elongate shaft 18 and liner 20 as indicated by the arrows.

Figure 1C:
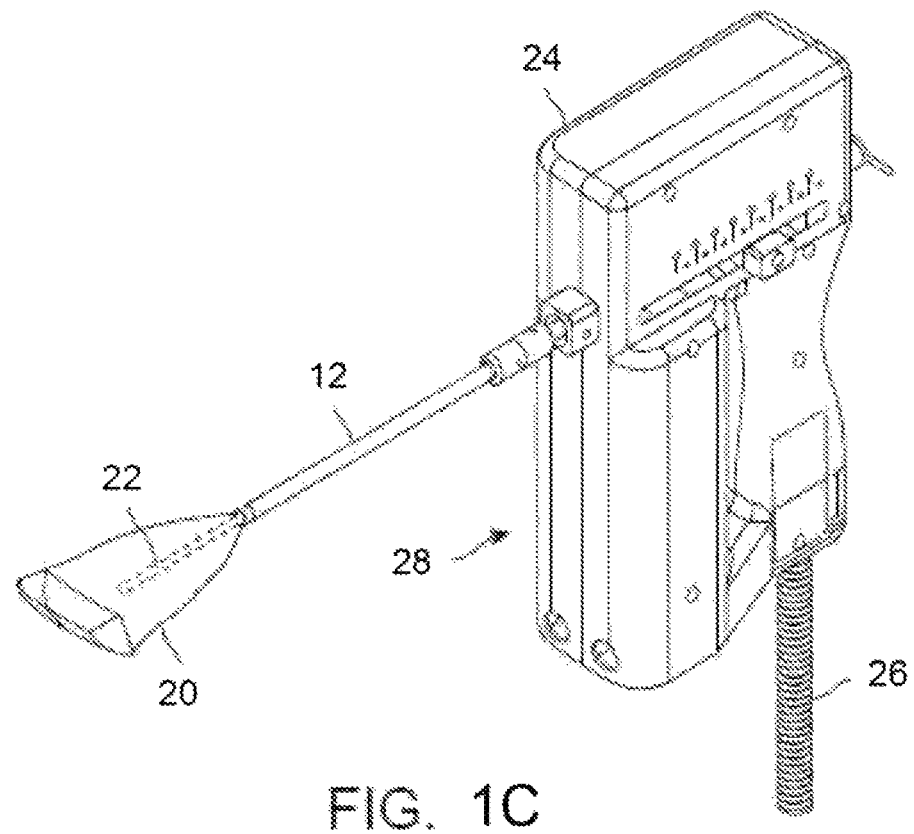
FIG. 1C shows a perspective view of a cryoablation assembly having a handle assembly which may integrate the electronics and pump assembly within the handle itself.

In another variation of the treatment assembly, FIG. 1C shows a perspective view of a cryoablation assembly having a handle assembly 24 which may integrate the electronics and pump assembly 28 within the handle itself. An exhaust tube 26 may also be seen attached to the handle assembly 24 for evacuating exhausted or excess cryoablative fluid or gas from the liner 20. Any of the cryoablative fluids or gases described herein may be utilized, e.g., compressed liquid-to-gas phase change of a compressed gas such as nitrous oxide ($N_2O$), carbon dioxide ($CO_2$), Argon, etc. The cooling probe 22 may be seen extending from sheath 12 while surrounded or enclosed by the liner or balloon 20. Hence, the handle assembly 24 with coupled cooling probe 22 and liner 20 may provide for a single device which may provide for pre-treatment puff-up or inflation of the liner 20, active cryoablation treatment, and/or post-treatment thaw cycles.

The handle assembly 24 may also optionally incorporate a display for providing any number of indicators and/or alerts to the user. For instance, an LCD display may be provided on the handle assembly 24 (or to a separate control unit connected to the handle assembly 24) where the display counts down the treatment time in seconds as the ablation is occurring. The display may also be used to provide measured pressure or temperature readings as well as any number of other indicators, symbols, or text, etc., for alerts, instructions, or other indications. Moreover, the display may be configured to have multiple color-coded outputs, e.g., green, yellow, and red. When the assembly is working through the ideal use case, the LED may be displayed as a solid green color. When the device requires user input (e.g. when paused and needing the user to press the button to re-start treatment) the LED may flash or display yellow. Additionally, when the device has faulted and treatment is stopped, the LED may flash or display a solid red color.

Figure 1D:
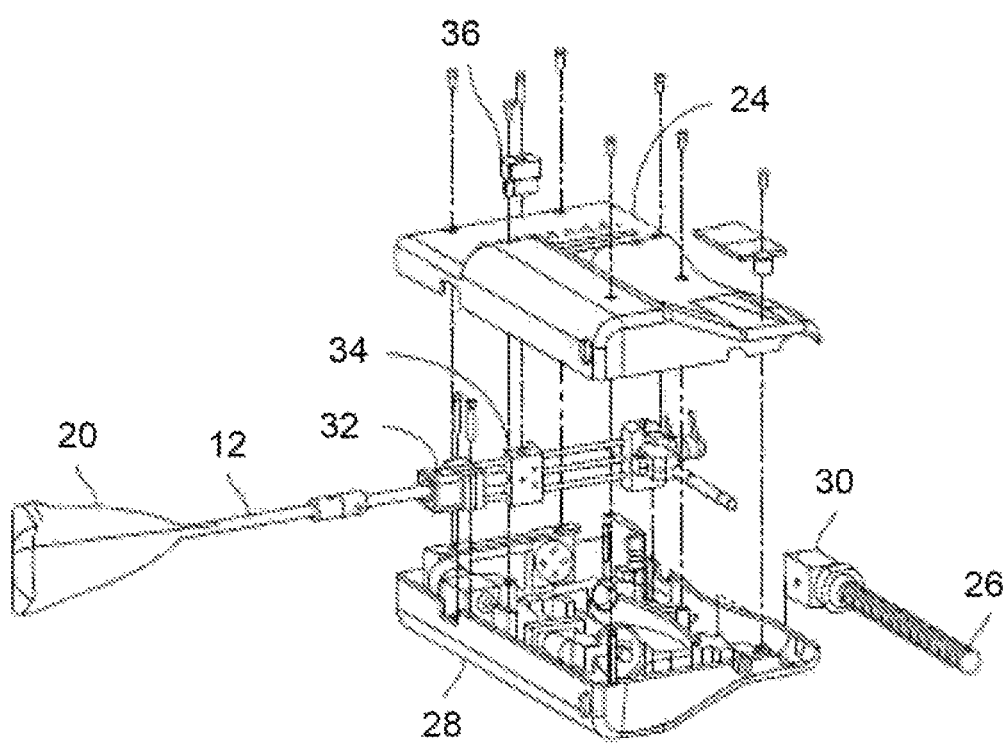
FIG. 1D shows the handle assembly in a perspective exploded view illustrating some of the components which may be integrated within the handle.

FIG. 1D shows the handle assembly 24 in a perspective exploded view to illustrate some of the components which may be integrated within the handle 24. As shown, the liner 20 and sheath 12 may be coupled to a sheath bearing assembly 32 and slider base block assembly 34 for controlling the amount of exposed treatment length along the cooling probe 22 (and as described in further detail below). An actuatable sheath control 36 may be attached to the slider base block assembly 34 for manually controlling the treatment length of the cooling probe 22 as well. Along with the electronics and pump assembly 28 (which may optionally incorporate a programmable processor or controller in electrical communication with any of the mechanisms within the handle 24), an exhaust valve 30 (e.g., actuated via a solenoid) may be coupled to the exhaust line 26 for controlling not only the outflow of the exhausted cryoablation fluid or gas but also for creating or increasing a backpressure during treatment, as described in further detail below.

Figure 1E:
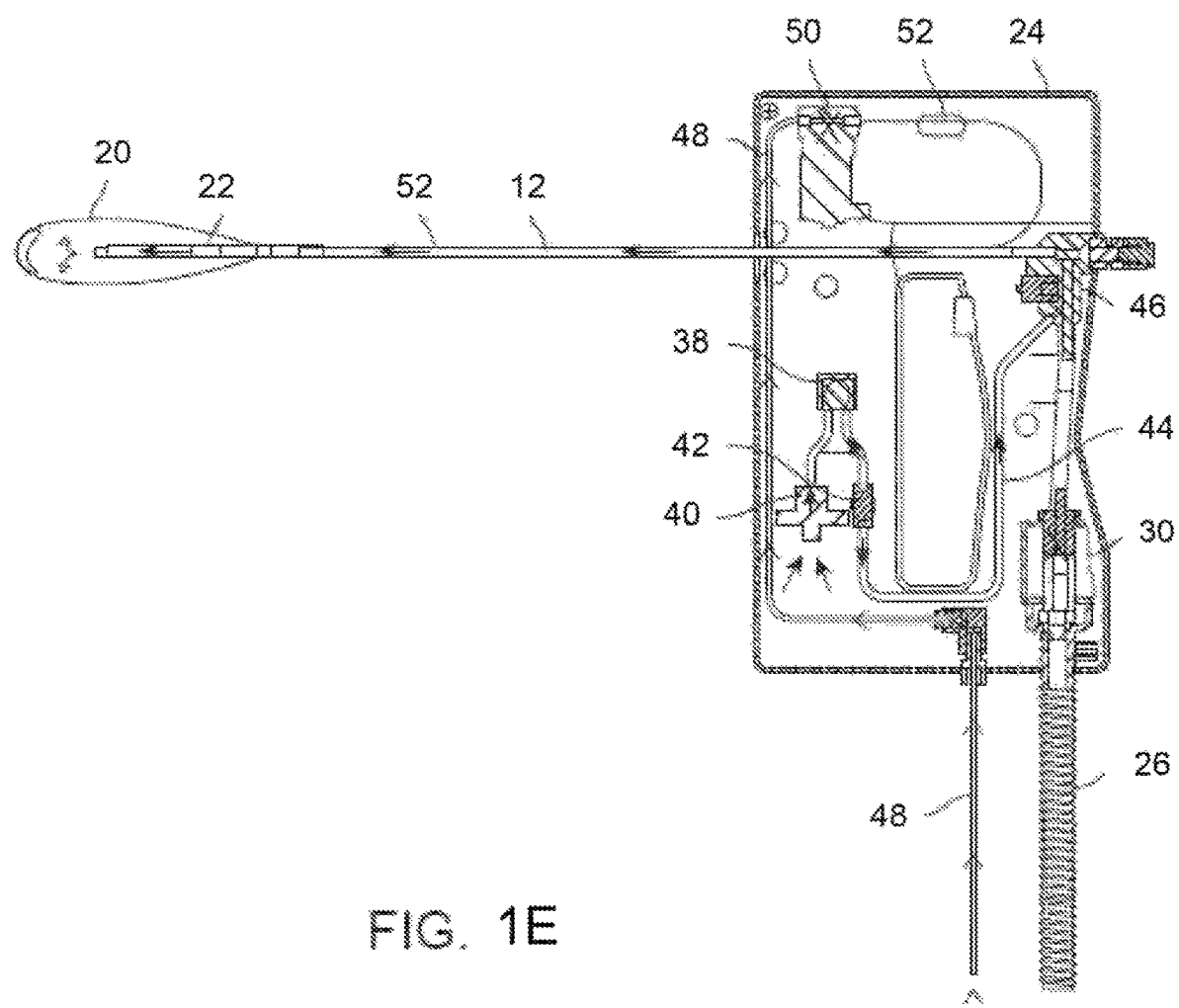
FIG. 1E shows an example of the system operation during a pre-treatment puff up process.
Figure 1F:
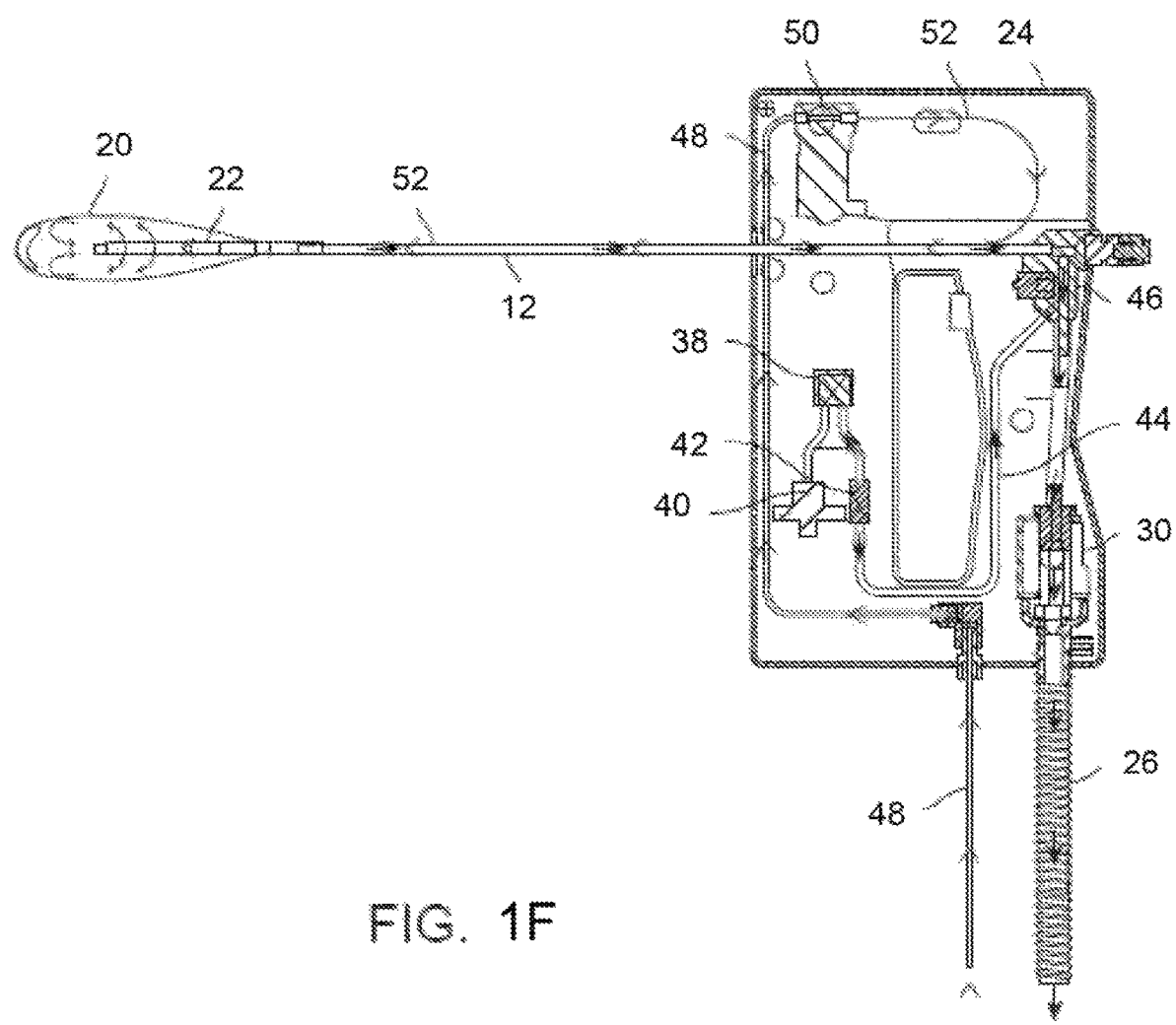
FIG. 1F shows an example of the system operation during a treatment process.
Figure 1G:
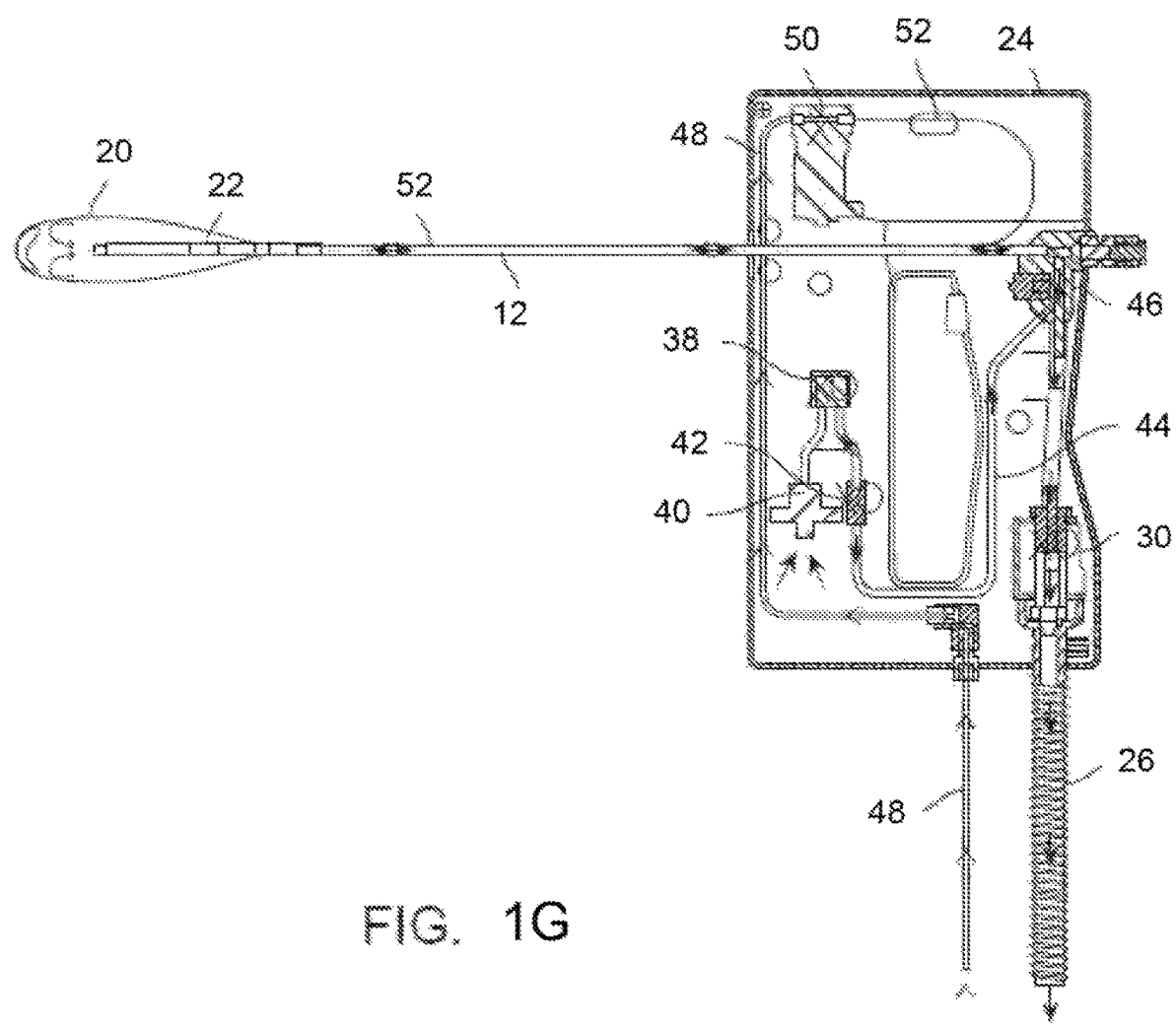
FIG. 1G shows an example of the system operation during a thawing and venting process.

In one example of how the handle assembly 24 may provide for treatment, FIGS. 1E to 1G illustrate schematic side views of how the components may be integrated and utilized with one another. As described herein, once the sheath 12 and/or liner 20 has been advanced and initially introduced into the uterus, the liner 20 may be expanded or inflated in a pre-treatment puff up to expand the liner 20 into contact against the uterine tissue surfaces in preparation for a cryoablation treatment. As illustrated in the side view of FIG. 1E, a pump 38 integrated within the handle assembly 24 may be actuated and a valve 42 (e.g., actuatable or passive) fluidly coupled to the pump 38 may be opened (as indicated schematically by an "O" over both the pump 38 and valve 42) such that ambient air may be drawn in through, e.g., an air filter 40 integrated along the handle 24, and passed through an air line 44 within the handle and to an exhaust block 46. The exhaust block 46 and air line 44 may be fluidly coupled to the tubular exhaust channel which extends from the handle 24 which is further attached to the cooling probe 22. As the air is introduced into the interior of the liner 20 (indicated by the arrows), the liner 20 may be expanded into contact against the surrounding uterine tissue surface.

A cryoablative fluid line 48 also extending into and integrated within the handle assembly 24 may be fluidly coupled to an actuatable valve 50, e.g., actuated via a solenoid, which may be manually closed or automatically closed (as indicated schematically by an "X" over the valve 50) by a controller to prevent the introduction of the cryoablative fluid or gas into the liner 20 during the pre-treatment liner expansion. An infusion line 52 may be fluidly coupled to the valve 50 and may also be coupled along the length of the sheath 12 and probe 22, as described in further detail below. The exhaust valve 30 coupled to the exhaust line 26 may also be closed (as indicated schematically by an "X" over the valve 30) manually or automatically by the controller to prevent the escape of the air from the exhaust block 46.

During this initial liner expansion, the liner 20 may be expanded in a gradual and controlled manner to minimize any pain which may be experienced by the patient in opening the uterine cavity. Hence, the liner 20 may be expanded gradually by metering in small amounts of air. Optionally, the pump 38 may be programmed and controlled by a processor or microcontroller to expand the liner 20 according to an algorithm (e.g., e.g. ramp-up pressure quickly to 10 mm Hg and then slow-down the ramp-up as the pressure increases to 85 mm Hg) which may be stopped or paused by the user. Moreover, the liner 20 may be expanded to a volume which is just sufficient to take up space within the uterine cavity. After the initial increase in pressure, the pressure within the liner 20 may be optionally increased in bursts or pulses. Moreover, visualization (e.g., via a hysteroscope or abdominal ultrasound) may be optionally used during the controlled gradual expansion to determine when the uterine cavity is fully open and requires no further pressurization. In yet another variation, the liner 20 may be cyclically inflated and deflated to fully expand the liner. The inflations and deflations may be partial or full depending upon the desired expansion.

In yet another alternative variation, the system could also use an amount of air pumped into the liner 20 as a mechanism for detecting whether the device is in a false passage of the body rather than the uterine cavity to be treated. The system could use the amount of time that the pump 38 is on to track how much air has been pushed into the liner 20. If the pump 38 fails to reach certain pressure levels within a predetermined period of time, then the controller may indicate that the device is positioned within a false passage.

There could also be a limit to the amount of air allowed to be pushed into the liner 20 as a way to detect whether the probe 22 has been pushed, e.g., out into the peritoneal cavity. If too much air is pushed into the liner 20 (e.g., the volume of air tracked by the controller exceeds a predetermined level) before reaching certain pressures, then the controller may indicate the presence of a leak or that the liner 20 is not fully constrained by the uterine cavity. The liner 20 may also incorporate a release feature which is configured to rupture if the liner 20 is not constrained such that if the system attempts to pump up the liner 20 to treatment pressure (e.g., 140 mmHg), the release feature will rupture before reaching that pressure.

Once the liner 20 has been expanded sufficiently into contact against the uterine tissue surface, the cryoablation treatment may be initiated. As shown in the side view of FIG. 1F, the air pump 38 may be turned off and the valve 42 may be closed (as indicated schematically by an "X" over the pump 38 and valve 42) to prevent any further infusion of air into the liner 20. With the cryoablative fluid or gas pressurized within the line 48, valve 50 may be opened (as indicated schematically by an "O" over the valve 50) to allow for the flow of the cryoablative fluid or gas to flow through the infusion line 52 coupled to the valve 50. Infusion line 52 may be routed through or along the sheath 12 and along the probe 22 where it may introduce the cryoablative fluid or gas within the interior of liner 20 for infusion against the liner 20 contacted against the surrounding tissue surface.

During treatment or afterwards, the exhaust valve 30 may also be opened (as indicated schematically by an "O" over the valve 30) to allow for the discharged fluid or gas to exit or be drawn from the liner interior and proximally through the cooling probe 22, such as through the distal tip opening. The fluid or gas may exit from the liner 20 due to a pressure differential between the liner interior and the exhaust exit and/or the fluid or gas may be actively drawn out from the liner interior, as described in further detail herein. The spent fluid or gas may then be withdrawn proximally through the probe 22 and through the lumen surrounded by the sheath 12, exhaust block 46, and the exhaust tube 26 where the spent fluid or gas may be vented. With the treatment fluid or gas thus introduced through infusion line 52 within the liner 20 and then withdrawn, the cryoablative treatment may be applied uninterrupted.

Once a treatment has been completed, the tissue of the uterine cavity may be permitted to thaw. During this process, the cryoablative fluid delivery is halted through the infusion line 52 by closing the valve 50 (as indicated schematically by an "X" over the valve 50) while continuing to exhaust for any remaining cryoablative fluid or gas remaining within the liner 20 through probe 22, through the lumen surrounded by sheath 12, and exhaust line 26, as shown in FIG. 1G. Optionally, the pump 38 and valve 42 may be cycled on and off and the exhaust valve 30 may also be cycled on and off to push ambient air into the liner 20 to facilitate the thawing of the liner 20 to the uterine cavity. Optionally, warmed or room temperature air or fluid (e.g., saline) may also be pumped into the liner 20 to further facilitate thawing of the tissue region.

As the spent cryoablative fluid or gas is removed from the liner 20, a drip prevention system may be optionally incorporated into the handle. For instance, a passive system incorporating a vented trap may be integrated into the handle which allows exhaust gas to escape but captures any vented liquid. The exhaust line 26 may be elongated to allow for any vented liquid to evaporate or the exhaust line 26 may be convoluted to increase the surface area of the exhaust gas tube to promote evaporation.

Alternatively, an active system may be integrated into the handle or coupled to the handle 24 where a heat sink may be connected to a temperature sensor and electrical circuit which is controlled by a processor or microcontroller. The heat sink may promote heat transfer and causes any liquid exhaust to evaporate. When the temperature of the heat sink reaches the boiling temperature of, e.g., nitrous oxide (around −86° C.), the handle may be configured to slow or stop the delivery of the cryoablative fluid or gas to the uterine cavity.

The pre-treatment infusion of air as well as the methods for treatment and thawing may be utilized with any of the liner, probe, or apparatus variations described herein. Moreover, the pre-treatment, treatment, or post-treatment procedures may be utilized altogether in a single procedure or different aspects of such procedures may be used in varying combinations depending upon the desired results.

Additionally and/or optionally, the handle 24 may incorporate an orientation sensor to facilitate maintaining the handle 24 in a desirable orientation for treatment. One variation may incorporate a ball having a specific weight covering the exhaust line 26 such that when the handle 24 is held in the desirable upright orientation, the treatment may proceed uninterrupted. However, if the handle 24 moved out of its desired orientation, the ball may be configured to roll out of position and trigger a visual and/or auditory alarm to alert the user. In another variation, an electronic gyroscopic sensor may be used to maintain the handle 24 in the desired orientation for treatment.

Figure 2A:
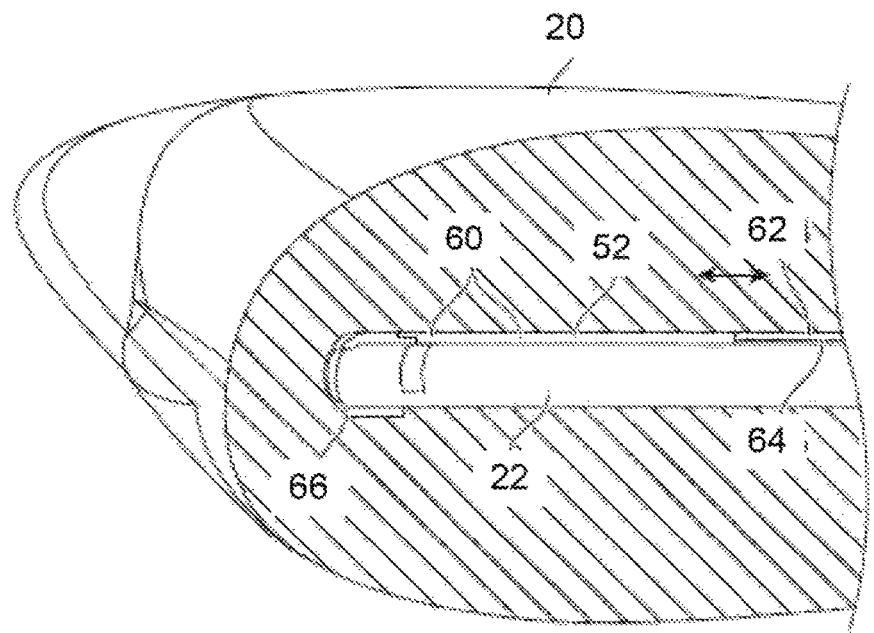
FIGS. 2A and 2B show cross-sectional side views of yet another variation of a cooling probe which utilizes a single infusion line in combination with a translatable delivery line.
Figure 2B:
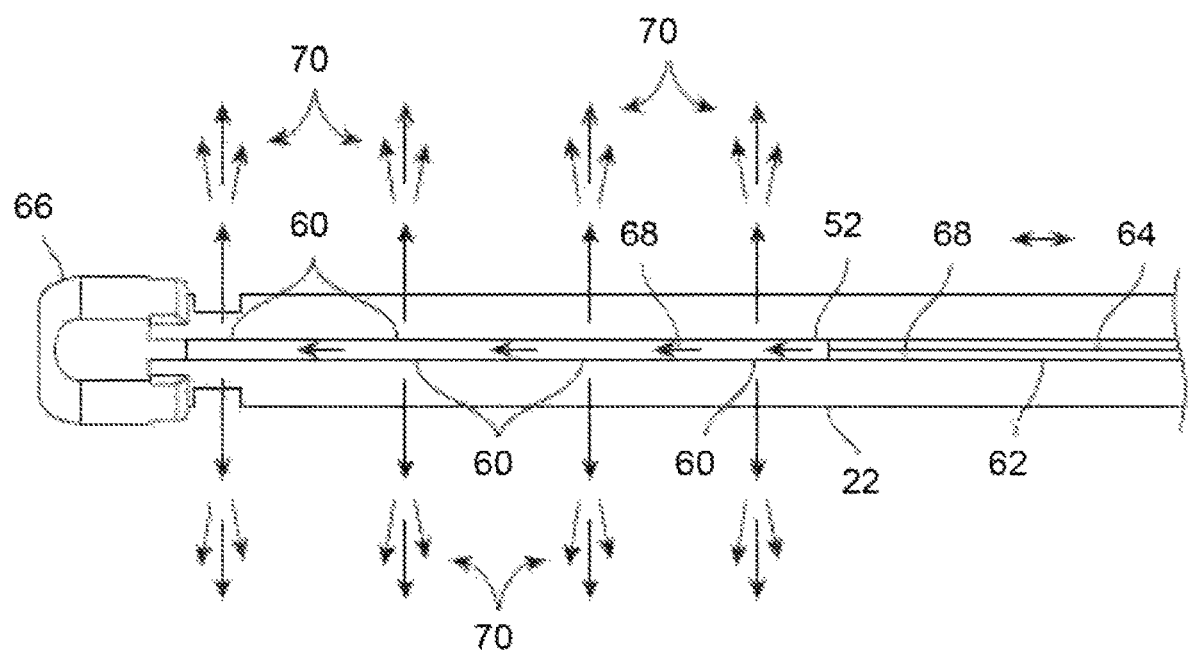

FIGS. 2A and 2B show cross-sectional side views of yet another variation of a cooling probe which utilizes a single infusion line in combination with a translatable delivery line. To accommodate various sizes and shapes of uterine cavities, the cooling probe may have a sliding adjustment that may be set, e.g., according to the measured length of the patient's uterine cavity. The adjustment may move along the sheath, along the exhaust tube as well as the delivery line within the infusion line. The sheath may constrain the liner 20 and also control its deployment within the cavity.

In this variation, an infusion line 52 (as described above) may pass from the handle assembly and along or within the sheath and into the interior of liner 20. The infusion line 52 may be aligned along the probe 22 such that the infusion line 52 is parallel with a longitudinal axis of the probe 22 and extends towards the distal tip 66 of the probe 22. Moreover, the infusion line 52 may be positioned along the probe 22 such that the line 52 remains exposed to the corners of the liner 20 which extend towards the cornua. With the infusion line 52 positioned accordingly, the length of the line 52 within the liner 20 may have multiple openings formed along its length which act as delivery ports for the infused cryoablative fluid or gas. A separate translating delivery line 64, e.g., formed of a Nitinol tube defining an infusion lumen therethrough, may be slidably positioned through the length of the infusion line 52 such that the delivery line 64 may be moved (as indicated by the arrows in FIG. 2A) relative to the infusion line 52 which remains stationary relative to the probe 22.

The openings along the length of the infusion line 52 may be positioned such that the openings are exposed to the sides of the interior of the liner 20, e.g., cross-drilled. As the cryoablative fluid or gas is introduced through the delivery line 64, the infused cryoablative fluid or gas 68 may pass through the infusion, line 52 and then out through the openings defined along the infusion line 52. By adjusting the translational position of the delivery line 64, the delivery line 64 may also cover a selected number of the openings resulting in a number of open delivery ports 60 as well as closed delivery ports 62 which are obstructed by the delivery line 64 position relative to the infusion line 52, as shown in the top view of FIG. 2B.

By translating the delivery line 64 accordingly, the number of open delivery ports 60 and closed delivery ports 62 may be adjusted depending on the desired treatment length and further ensures that only desired regions of the uterine tissue are exposed to the infused cryoablative fluid or gas 68. Once the number of open delivery ports 60 has been suitably selected, the infused cryoablative fluid or gas 68 may bypass the closed delivery ports 62 obstructed by the delivery line 64 and the fluid or gas may then be forced out through the open delivery ports 60 in a transverse direction as indicated by the infusion spray direction 70. The terminal end of the infusion line 52 may be obstructed to prevent the distal release of the infused fluid or gas 68 from its distal end. Although in other variations, the terminal end of the infusion line 52 may be left unobstructed and opened.

Figure 3A:
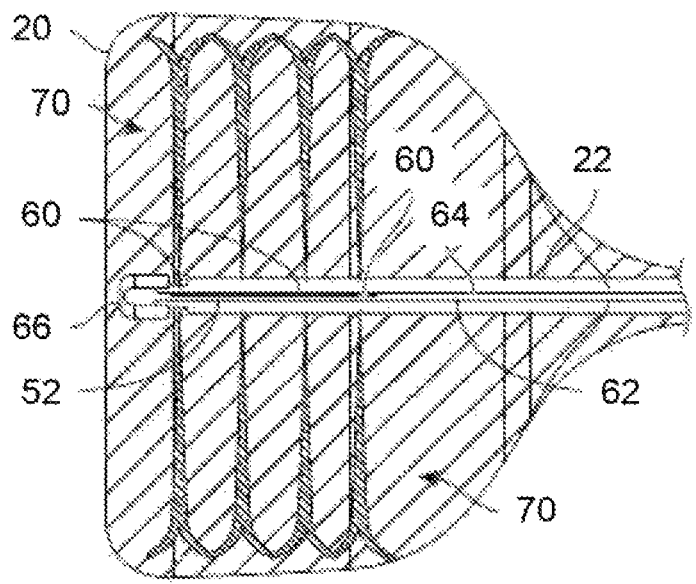
FIGS. 3A and 3B show top and perspective views of the expanded liner with four pairs of the open delivery ports exposed in apposed direction.
Figure 3B:
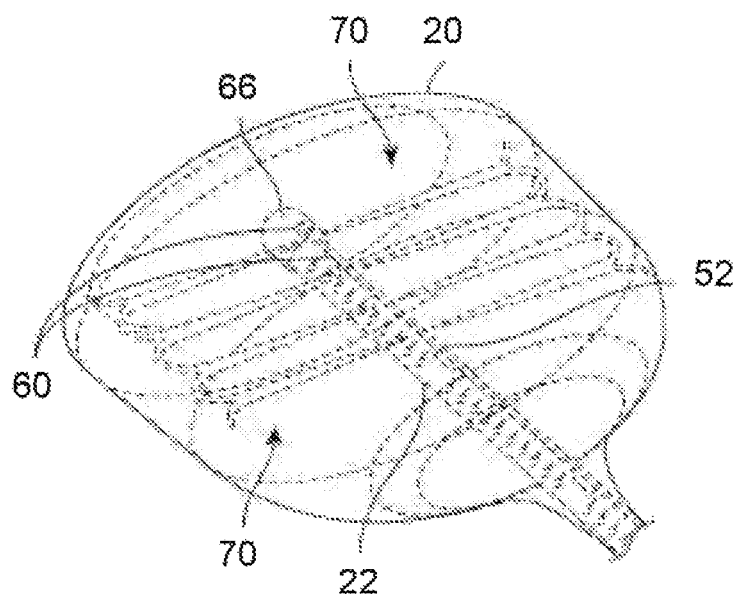

FIGS. 3A and 3B show top and perspective views of the expanded liner 20 with four pairs of the open delivery ports 60 exposed in apposed direction. Because the infused fluid or gas 68 may be injected into the liner 20, e.g., as a liquid, under relatively high pressure, the injected cryoablative liquid may be sprayed through the open delivery ports 60 in a transverse or perpendicular direction relative to the cooling probe 22. The laterally infused cryoablative fluid 70 may spray against the interior of the liner 20 (which is contacted against the surrounding tissue surface) such that the cryoablative liquid 70 coats the interior walls of the liner 20 due to turbulent flow causing heavy mixing. As the cryoablative liquid 70 coats the liner surface, the sprayed liquid 70 may absorb heat from the tissue walls causing rapid cooling of the tissue while also evaporating the liquid cryogen to a gas form that flows out through the cooling probe 22. This rapid cooling and evaporation of the cryoablative liquid 70 facilitates the creation of a fast and deep ablation over the tissue. During treatment, the temperature within the cavity typically drops, e.g., −86° C., within 2-3 seconds after the procedure has started. While the interior walls of the liner 20 are first coated with the cryoablative liquid 70, a portion of the cryoablative liquid 70 may no longer change phase as the procedure progresses.

While four pairs of the open delivery ports 60 are shown, the number of exposed openings may be adjusted to fewer than four pairs or more than four pairs depending on the positioning of the delivery line 64 and also the number of openings defined along the infusion line 52 as well as the spacing between the openings. Moreover, the positioning of the openings may also be adjusted such that the sprayed liquid 70 may spray in alternative directions rather than laterally as shown. Additionally and/or alternatively, additional openings may be defined along other regions of the infusion line 52.

Further variations of the treatment assembly features and methods which may be utilized in combination with any of the features and methods described herein may be found in the following patent applications:

U.S. patent application Ser. No. 13/361,779 filed Jan. 30, 2012 (US Pub. 2012/0197245);

U.S. patent application Ser. No. 13/900,916 filed May 23, 2013 (US Pub. 2013/0296837):

U.S. patent application Ser. No. 14/019,898 filed Sep. 6, 2013 (US Pub. 2014/0012156);

U.S. patent application Ser. No. 14/019,928 filed Sep. 6, 2013 (US Pub. 2014/005648);

U.S. patent application Ser. No. 14/020,265 filed Sep. 6, 2013 (US Pub. 2014/0005649);

U.S. patent application Ser. No. 14/020,306 flied Sep. 6, 2013 (US Pub. 2014/0025055);

U.S. patent application Ser. No. 14/020,350 filed Sep. 6, 2013 (US Pub. 2014/0012244);

U.S. patent application Ser. No. 14/020,397 filed Sep. 6, 2013 (US Pub. 2014/0012243);

U.S. patent application Ser. No. 14/020,452 filed Sep. 6, 2013 (US Pub. 2014/0005650);

U.S. patent application Ser. No. 14/086,050 filed Nov. 21, 2013 (US Pub. 2014/0074081);

U.S. patent application Ser. No. 14/086,088 filed Nov. 21, 2013 (US Pub. 2014/0088579);

U.S. patent application Ser. No. 14/029,641 filed Sep. 17, 2013 (US Pub. 2015/0080869); and U.S. patent application Ser. No. 14/265,799 filed Apr. 30, 2014 (US Pub. 2015/0289920).

Each of the patent applications above is incorporated herein by reference in its entirety and for any purpose herein.

Figure 4A:
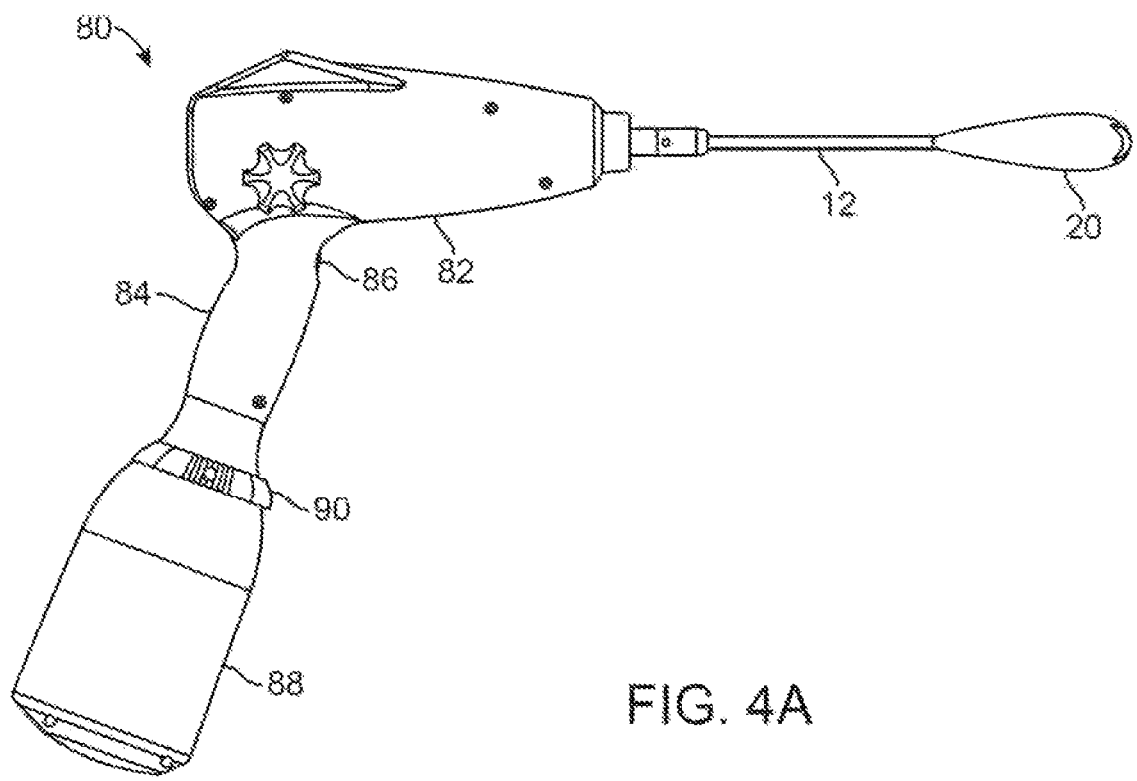
FIGS. 4A to 4C show side and assembly views of another variation of the treatment assembly.
Figure 4B:
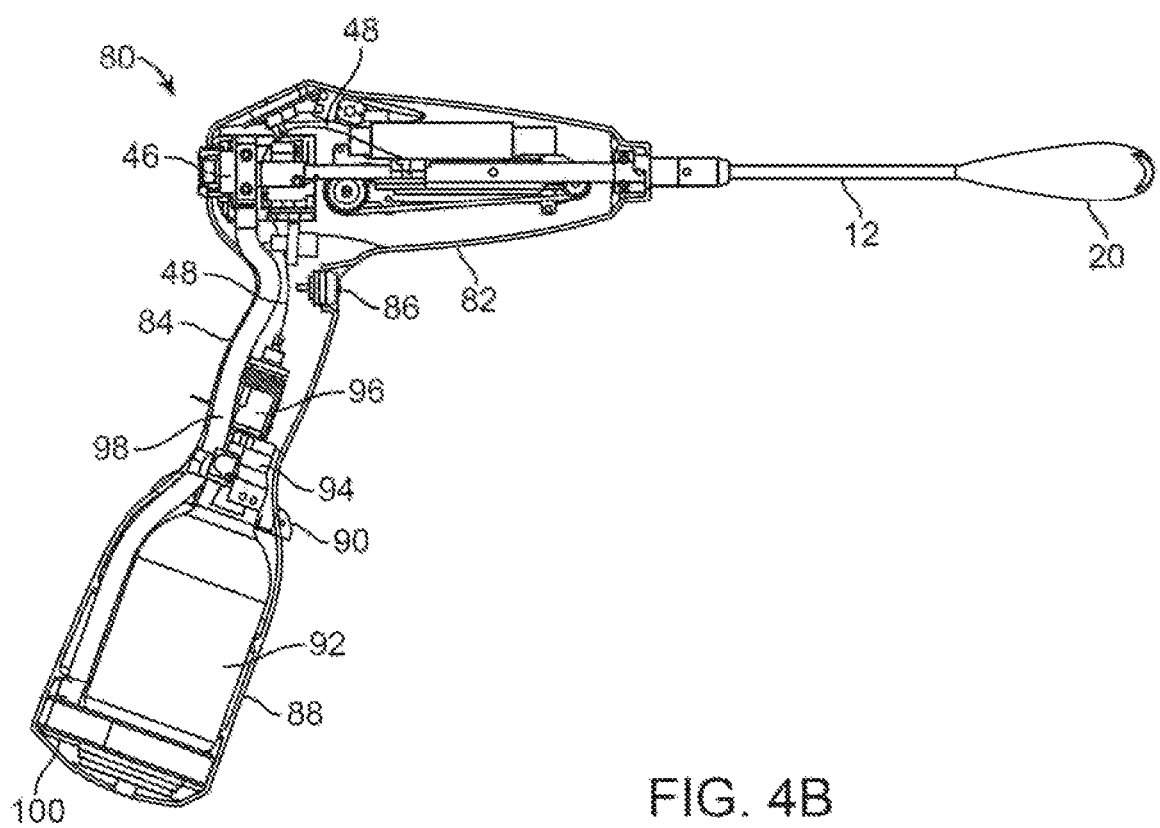
Figure 4C:
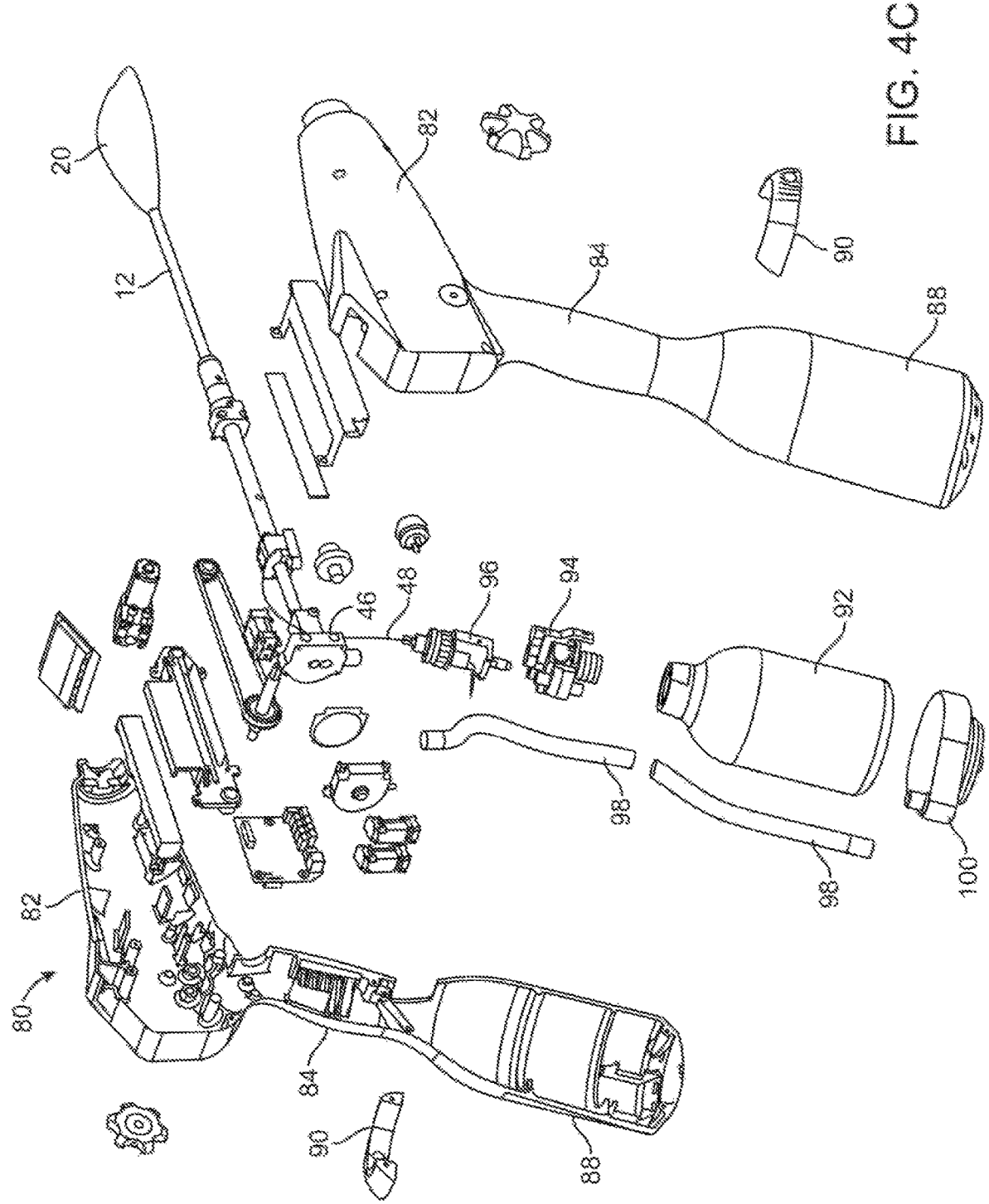

Yet another variation of the treatment assembly 80 is shown in the side and partial cross-sectional side views of FIGS. 4A and 4B which illustrate a housing 82 having a handle 84 and a reservoir housing 88 extending from and attached directly to the handle 84. FIG. 4C further illustrates a perspective assembly view of the treatment assembly 80 and some of its components contained internally.

The sheath 12 having the liner 20 may extend from the housing 82 while an actuator 86 may be located, for instance, along the handle 84 to enable the operator to initiate the cryoablative treatment. A reservoir or canister 92 fully containing the cryoablative agent (as described herein) may be inserted and retained within the reservoir housing 88. The reservoir housing 88 and/or the handle 84 may further incorporate a reservoir engagement control 90 which may be actuated, e.g., by rotating the control 90 relative to the handle 84, to initially open fluid communication with the reservoir or canister 92 to charge the system for treatment.

The reservoir or canister 92 may be inserted into the reservoir housing 88 and into secure engagement with a reservoir or canister valve 94 which may be coupled to the reservoir engagement control 90. The valve 94 may be adjusted to open the reservoir or canister 92 for treatment or for venting of the discharged cryoablative agent during or after treatment. An inflow modulation control unit 96 (e.g., an actuatable solenoid mechanism) may be coupled directly to the reservoir or canister valve 94 and the cryoablative fluid line 48 may be coupled directly to the modulation control unit 96 and through the sheath 12 and into fluid communication within the liner 20, as described herein.

During or after treatment, the discharged cryoablative fluid may be evacuated through the exhaust block 46 contained within the housing and then through the exhaust line 98 coupled to the exhaust block 46. The exhaust line 98 may extend through the handle 84 and the reservoir housing 88 and terminate at an exhaust line opening 100 which may be attached to another exhaust collection line.

Figure 5A:
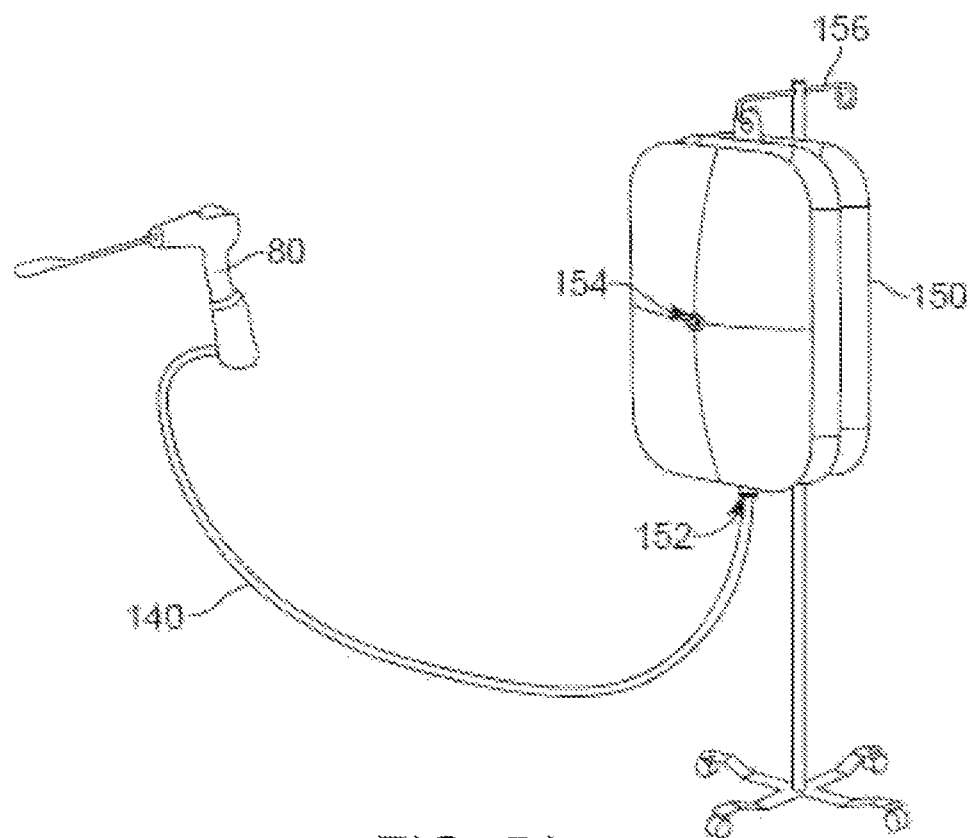
FIGS. 5A and 5B show examples of collection systems which can be used to collect the discharged liquid or gas.
Figure 5B:
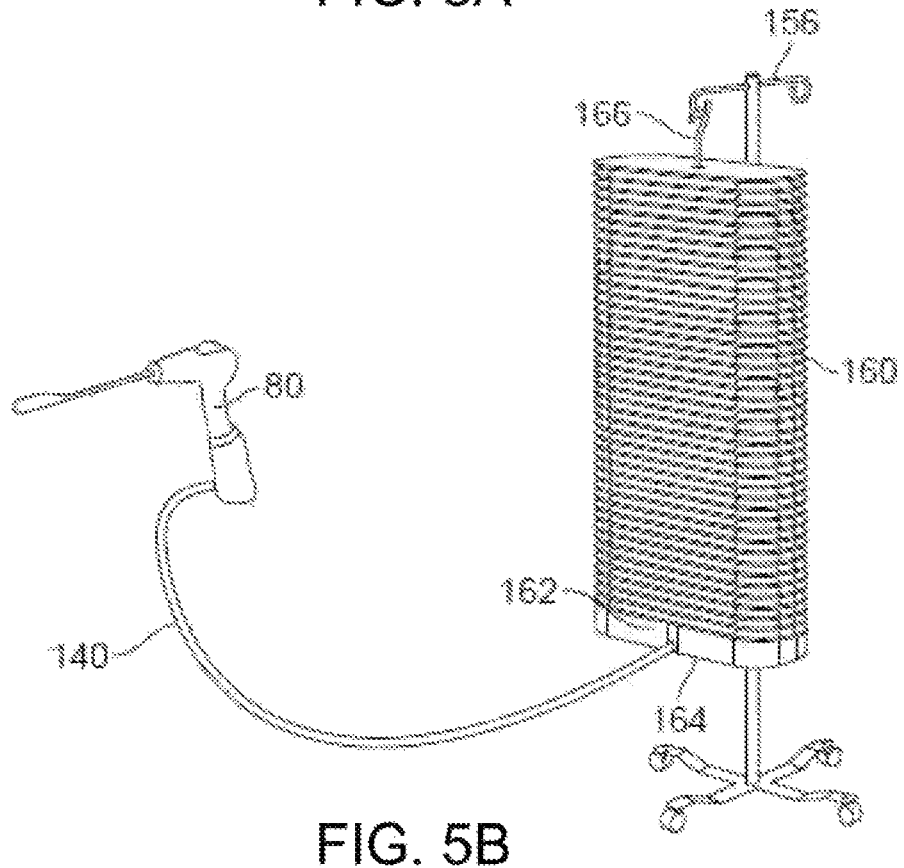

With the discharged cryoablative agent in a completely gaseous state, the evacuating exhaust line 140 may be vented to the surrounding environment or optionally coupled to a scavenging system to collect the discharged gas to limit exposure. FIGS. 5A and 5B show assembly views of examples of collection bags which may be optionally used with the treatment assembly. Scavenging systems may incorporate features such as orifices or valves to prevent any vacuum applied by the scavenging unit from interfering with the backpressure within the treatment device.

FIG. 5A shows an inflating collection bag 150 which is expandable in width coupled to the evacuating exhaust line 140 via a disconnect valve 152 (e.g., unidirectional valve). The collection bag 150, which may be reusable or disposable, may be supported via a pole 156 and may also incorporate a release plug 154 which may allow for the venting of the collected gas during or after a treatment procedure is completed.

Similarly, FIG. 5B shows an accordion-type collector 160 also supported via a pole 156 and a connector 166 attached to the collector 160. The evacuating exhaust line 140 may be removably coupled to the collector 160 via a disconnect valve 162 (e.g., unidirectional valve) and may also incorporate a release plug 164 for venting any collected gas during or after a treatment procedure. The vertically-expanding collector 160 may define a hollow passageway through the center of the vertical bellows which allows for the connector 166 (e.g., rigid rod or flexible cord) to pass through and support the base of the collector 160. The connector 166 also prevents the collector 160 from falling over to a side when inflating. As the gas enters through the bottom of the collector 160, the bellow may inflate upward.

Figure 6:
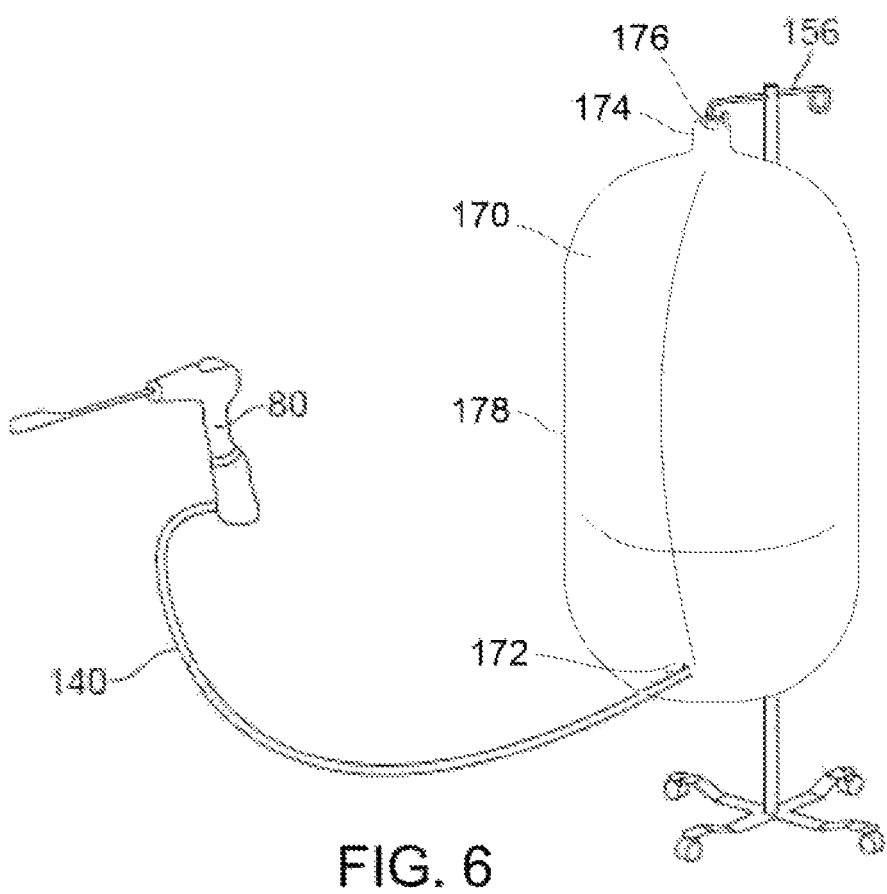
FIG. 6 shows another example of collection system utilizing a bag for collecting the discharged liquid or gas.

In yet another variation, FIG. 6 shows an exhaust collection bag 170 which may also be supported by the pole 156. The evacuating exhaust line 140 may be removably coupled to the collection bag 170 via a tubing connector 172 located near or at a bottom of the collection bag 170. The bag 170 itself may be formed from two layers of a lubricious materials which are attached or welded (e.g., RF dielectric welded) around its periphery along its edges 178. Moreover, the collection bag 170 may be configured to form an extension 174 which projects from the bag 170 and forms an opening 176 for passing a hook through or to provide a point for attachment. This opening may be reinforced to support. e.g., 2 lbs for at least 1 hour. The collection bag 170 may be designed to hang, e.g., from an IV pole as shown such that it is maintained off the floor to keep it clean should a user want to reuse it a number of times.

The bag 170 may be fabricated from, e.g., a polyurethane film, selected for its lubricity, elasticity, clarity, low cost and ability to be RF dielectric welded. Such polyurethane films may be commercially available from API Corporation (DT 2001-FM). The film may have a thickness of, e.g., 0.003 inches. Because the bag 170 inflates at relatively low pressures, the lubricity of the layers prevents the layers of film from sticking together and allows the bag to readily inflate. Also, to accommodate potential volume increases associated with increased temperatures, the bag 170 material also exhibits elasticity, e.g., film elongation may be on the order of 800%. The bag may be fabricated to have a burst pressure of at least greater than or equal to, e.g., ≥3 psi. The bag 170 may also be fabricated so as to be at least partially transparent so that the clarity of the bag results in an object that visually occupies less space in the procedure room because objects can be seen through it.

Figure 7A:
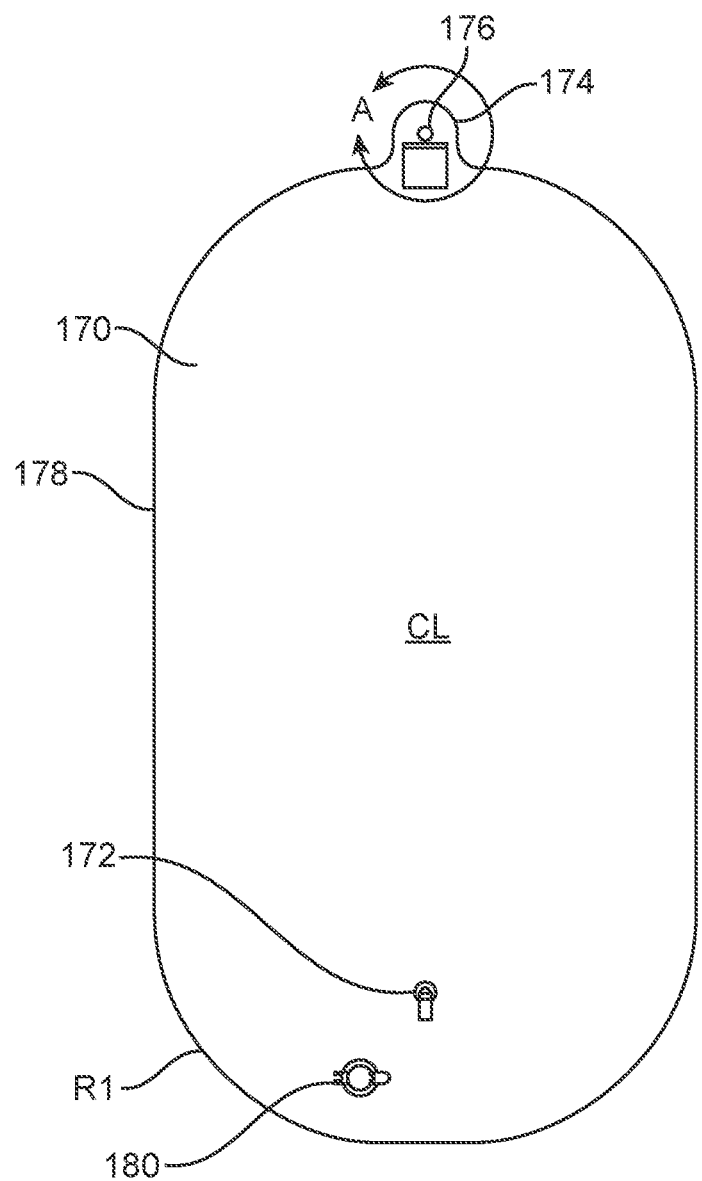
FIGS. 7A and 7B show respective front and detail views of the collection bag in a flattened configuration.
Figure 7B:
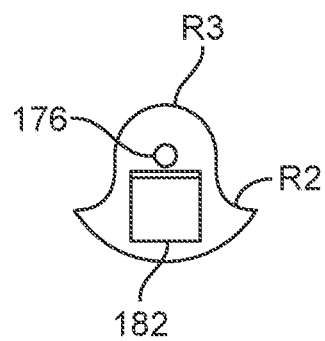

FIG. 7A shows a collection bag 170 when flattened (e.g., when deflated prior to use) for illustrative purposes and FIG. 7B shows a detail view of the extension 174. As shown, bag 170 may be formed to include tubing connector 172 which may be positioned near or at a bottom of the bag 170 when hanging during use. The bag 170 may be formed with rounded or curved corners having a radius R1, e.g., 11.0 inches, around all four of its corners so as to facilitate exhaust gas infusion and removal from the bag interior volume.

When flattened, the bag 170 may measure in one variation, e.g., 25 inches in width and 45.5 inches in length. The tubing connector 172 may be located along a centerline CL of the bag 170 which may also incorporate a drain closure 180 which may be opened to facilitate the removal of any collected exhaust gases within the bag 170 after the conclusion of a treatment procedure. The tubing connector 172 may be located, e.g., 7.0 inches from the bottom of the bag 170, while the drain closure 180 may be located, e.g., 3.1 inches from the bottom and 3.0 inches from the centerline CL. While the connector 172 and drain closure 180 are located on the same side of the bag 170, they may also be located on opposite sides or along the sides of the bag 170, if so desired. Moreover, the tubing connector 172 may incorporate a valve and also be configured as a quick disconnect fitting which allows the user to connect the exhaust line 140 during a procedure to collect the exhaust gas and to also prevent the outflow of gas when disconnected from the bag 170 at the end of the treatment.

Additionally and/or optionally, the collection bag 170 may be configured with two vent ports to enable it to be vented either manually or via wall suction. To facilitate wall suction, an extra quick disconnect adapter may be provided and stored in pouch 182 at the top of the bag 170. The user may simply push the quick disconnect onto the suction tubing (connected on the other end to wall suction) and then connect the quick disconnect fitting into the tubing connector 172 on the collection bag. The manual vent port may simply comprise the drain closure 180 that can be pulled-out by the user. The drain closure 180 may be positioned near or at the bottom of the bag 170 to reduce the user's exposure to $N_2O$ while emptying the bag 170. Locating the drain closure 180 at the bottom of the bag 170 also enables the user to roll the bag from top down to empty it.

The extension 176, shown in the detail view of FIG. 7B, may be formed with an optional pouch 182 and may also form a radius R2, e.g., 1.0 inches, between the bag 170 and extension 176 and a radius R3, e.g., 1.5 inches, around the extension 176 itself.

Figure 8A:
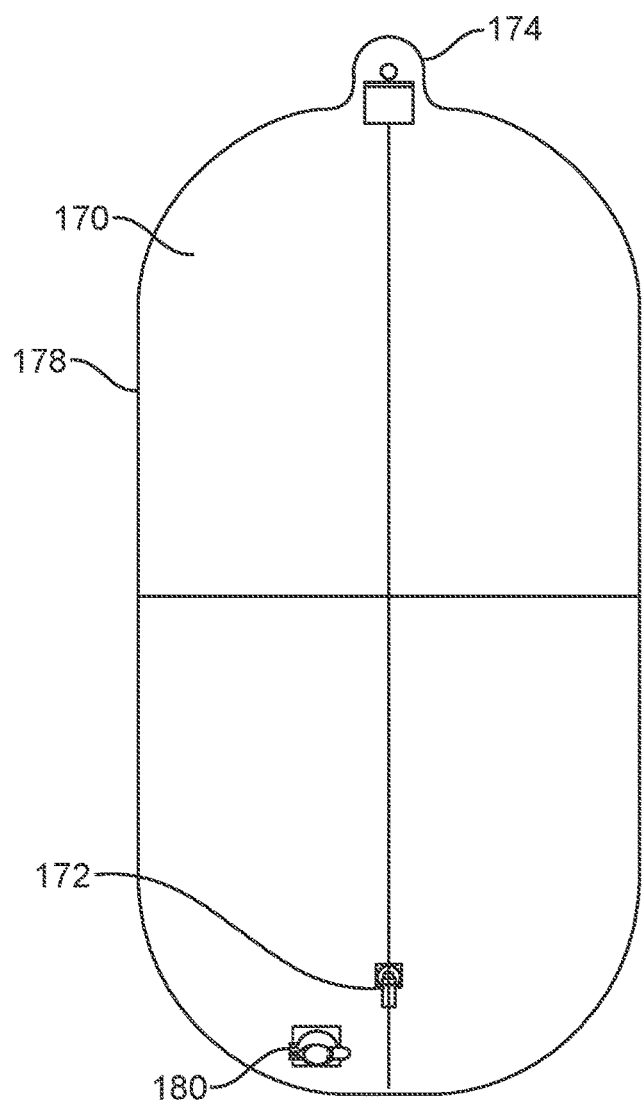
FIGS. 8A and 8B show front and side views of the collection bag in an expanded configuration.
Figure 8B:
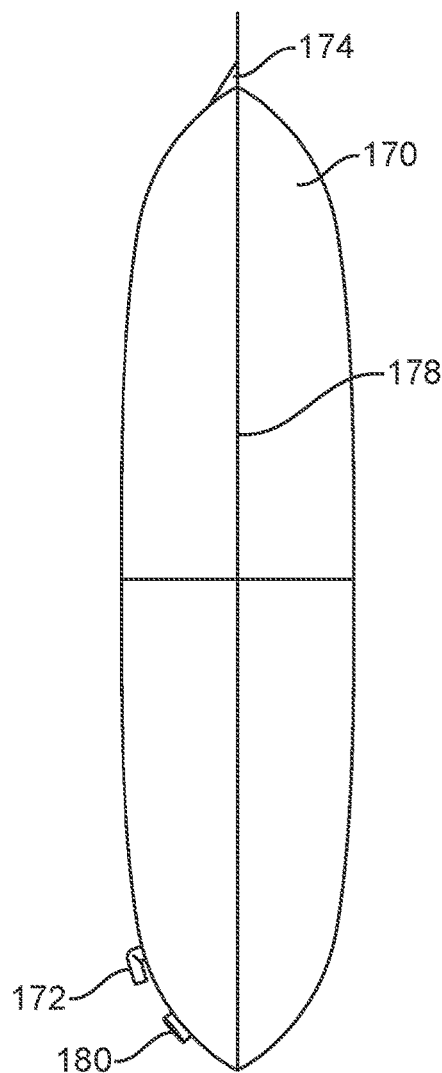

FIGS. 8A and 8B show respective front and side views of the bag 170 in its inflated state. When filled with the exhaust gas, bag 170 may expand such its width and length reduces, e.g., 21.0 inches in width and 41.5 inches in length. Moreover, the layers of material forming the bag 170 may also separate from one another forming a height of thickness of, e.g., 10.0 inches, when fully expanded.

Making the bag 170 over-sized lengthwise further allows the volume to be distributed in such a way that it is less intrusive in the procedure room. A shorter, wider collection bag occupies more space where people and other equipment are often located. The size and shape of the bag 170 make it easier to manually transport and, if necessary, to open and vent the hag 170 outside.

Aside from the bag 170 itself, the tubing connector 172 may also incorporate a number of features to facilitate emptying of the bag 170. As the bag 170 is evacuated via an external suction source, a first side 192A of the bag 170, e.g., the layer of the bag 170 where the tubing connector 172 is positioned, and a second side 192B of the bag 170, e.g., the layer of the bag 170 opposite to the first side 192A, may collapse upon itself and adhere to one another particularly around the area of the bag where the tubing connector 172 is positioned thereby trapping exhaust gas in the remainder of the bag 170 and preventing it from evacuating.

Figure 9:
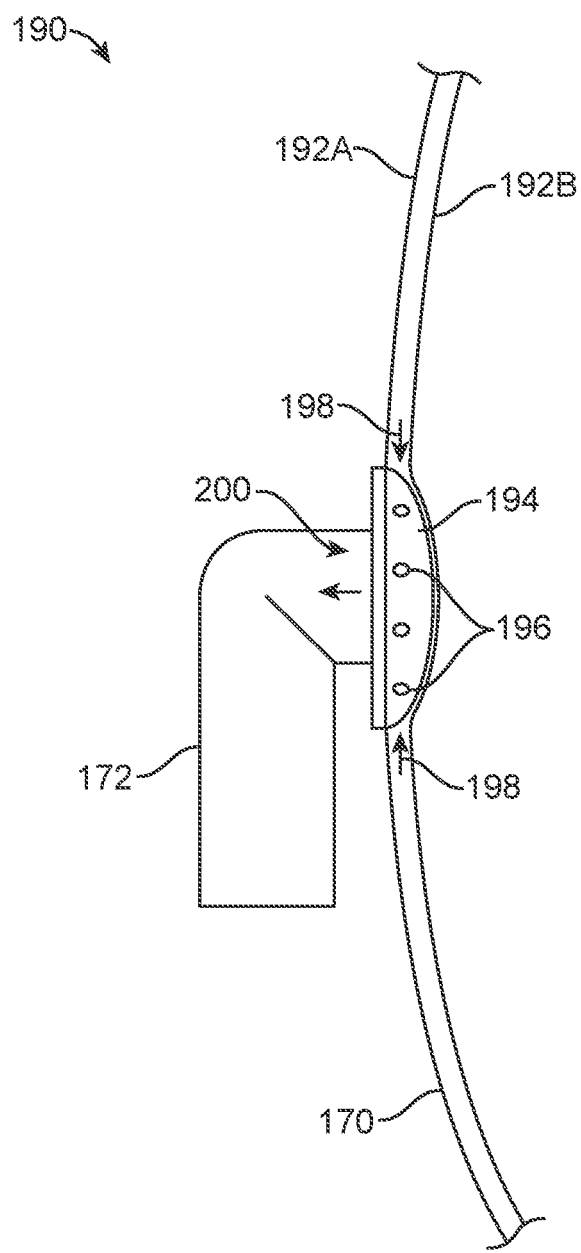
FIG. 9 shows a side view of a support member having a gentle dome-shaped or curved structure defining one or more openings along its surface.

One example of an apparatus for facilitating evacuation is shown in the side view of FIG. 9 which illustrates assembly 190. The tubing connector 172 may incorporate a support member 194 having a contact surface which has a gentle dome-shaped or curved structure defining one or more openings 196 along its surface, e.g., around a periphery of the member 194. The member 194 may extend from the tubing connector 172 and into the interior of the bag 170. The interior of the member 194 may allow for fluid communication through the openings 196 and a channel 200 defined through the member 194. In use, as the layers 192A, 192B collapse, the member 194 may function as a tenting structure which prevents the layers 192A, 192B from fully adhering to one another and thereby maintaining formed channels 198 around the member 194. These channels 198 allow for the trapped gas to pass through the openings 196, into the channel 200, and out the tubing connector 172. The support member 194 may be fabricated from any number of structurally robust materials, e.g., plastics, polymers, metals, etc.

This support member or any of the support members described herein may be used in any number of combinations with any of the other features described herein.

Figure 10A:
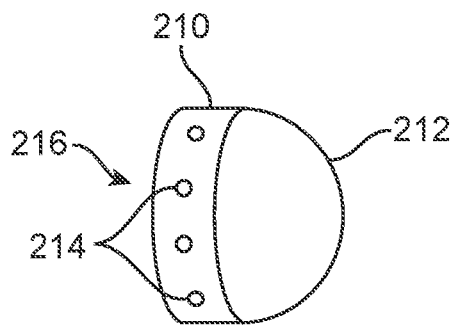
FIGS. 10A and 10B show perspective and side views of another variation of the support member which has a dome-shaped feature formed in a hemi-spherical shape.
Figure 10B:
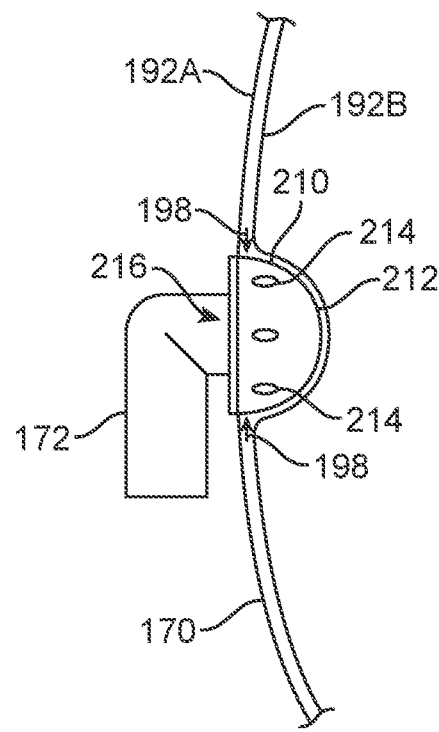

FIG. 10A shows a perspective view of another variation of the support member 210 which has a dome-shaped feature 212 formed in a hemi-spherical shape. The one or more openings 214 may be formed around a periphery of the member 210 with the channel 216 fluidly in communication through the member 210. FIG. 10B shows a side view of the support member 210 attached to the tubing connector 172 within the bag interior and the formed channels 198 around the periphery of the member 210.

Figure 11A:
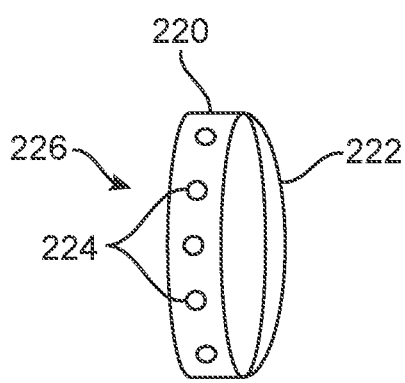
FIGS. 11A and 11B show perspective and side views of another variation of the support member having a curved interface member which extends beyond a periphery of the support member where the one or more openings are defined.
Figure 11B:
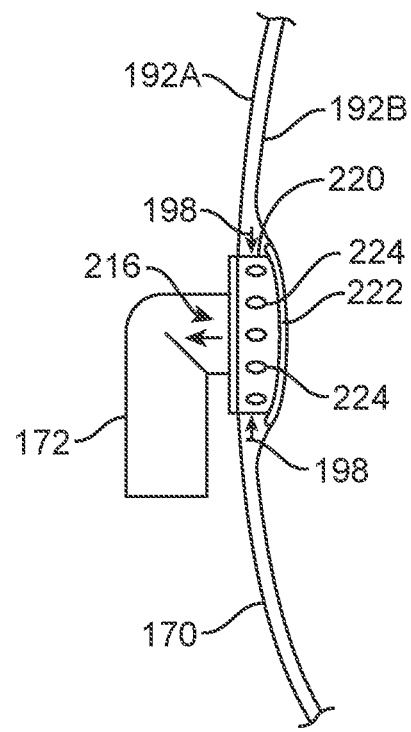

FIG. 11A shows a perspective view of another variation of the support member 220 having a curved interface member 222 which extends beyond a periphery of the support member 220 where the one or more openings 224 are defined. FIG. 11B shows a side view of the support member 220 and illustrates how the curved interface member 222 maintains the formed channel 198 for evacuating the gas through the openings 224 and through the channel 226.

Figure 12A:
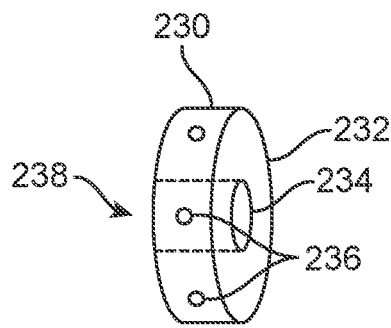
FIGS. 12A and 12B show perspective and side views of yet another variation where the support member has a curved surface but also defines an opening or lumen extending through the member.
Figure 12B:
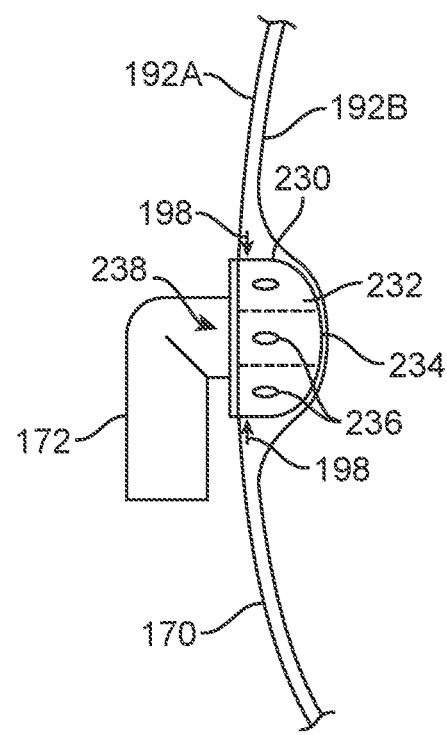

FIG. 12A shows a perspective view of yet another variation where the support member 230 has a curved surface 232 but also defines an opening or lumen 234 extending through the member 230. The side view of FIG. 12B illustrates how the opening or lumen 234 may help to pull the second layer 192B into the opening to help pull and/or retain the layer material to maintain the openings 236 unobstructed for evacuating the exhaust gas through the openings 236 and channel 238.

Figure 13A:
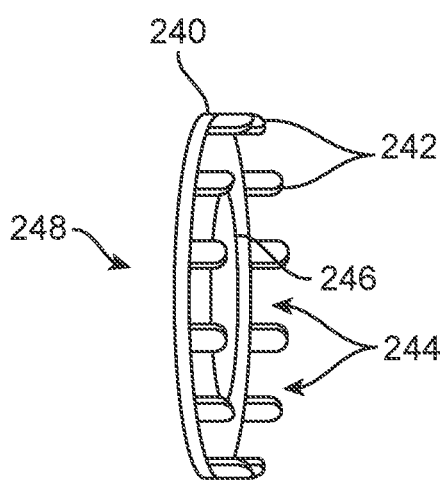
FIGS. 13A and 13B show perspective and side views of yet another variation where the support member may be formed of a peripheral member having one or more extensions formed around a periphery of the member and projecting away from the support member.
Figure 13B:
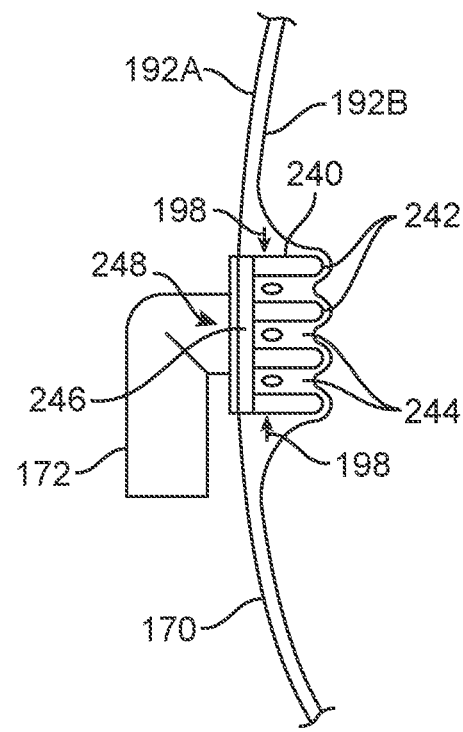

FIG. 13A shows a perspective view of yet another variation where the support member 240 may be formed of a peripheral member having one or more extensions 242 formed around a periphery of the member and projecting away from the support member 240 to form one or more corresponding channels 244 between the extensions 242. The side view of FIG. 13B shows the support member 240 attached to the tubing connector 172 such that the one or more extensions 242 extend away from the member 240 and into the interior of the bag. The one or more extensions 242 functions to tent the material of the bag such that the exhaust gas may exit through the channels 244 and out through the channel 246.

Figure 14A:
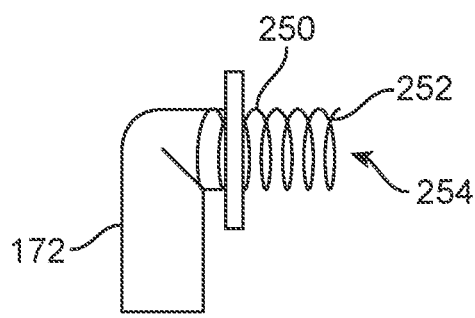
FIGS. 14A and 14B show side views of yet another support member formed as a helical member or spring forming a channel and extending away from the tubing connector.
Figure 14B:
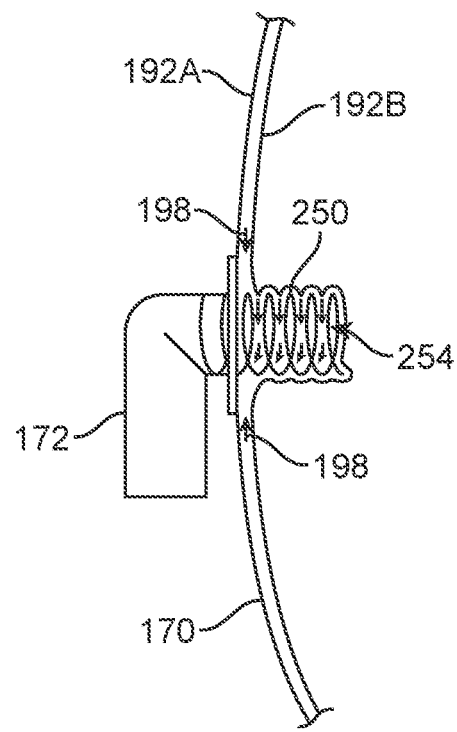

FIG. 14A shows a side view of yet another support member 250 formed as a helical member or spring forming a channel 254 and extending away from the tubing connector 172. The distal tip 252 of the member 250 may be formed to be atraumatic so that as the layer 192B collapses onto the member 250, the distal tip 252 is inhibited from piercing through the bag 170, as shown in the side view of FIG. 14B. The channel 254 may remain clear of the layer material thereby allowing the exhaust gas from exiting through the channel 254 and out the tubing connector 172.

Figure 15A:
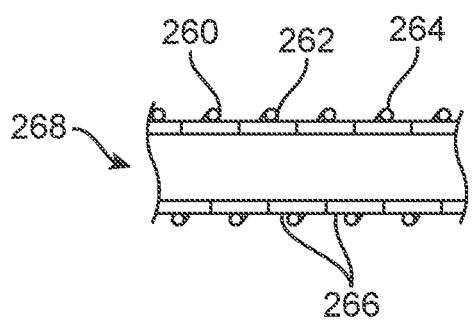
FIGS. 15A and 15B show cross-sectional side views of yet another variation of a support member which is formed as a flexible convoluted or perforated tube having a helically-shaped projection formed along the outer surface of the tube.
Figure 15B:
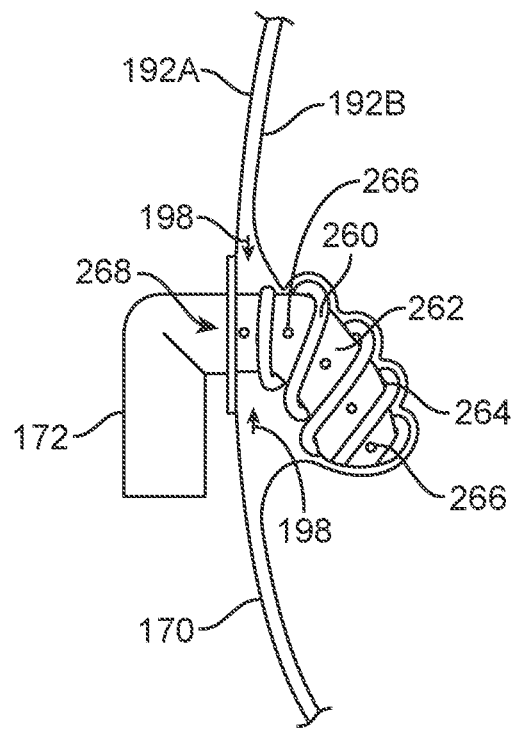

FIG. 15A shows a cross-sectional side view of yet another variation of a support member 260 which is formed as a flexible convoluted or perforated tube 262 having a helically-shaped projection 264 formed along the outer surface of the tube 262. The tube 262 may also define one or more openings 266 through the surface of the tube 262 so that the openings 266 extend into the channel 268 formed through the length of the tube 262. FIG. 15B shows how the projection 264 may prevent the layer material 192B from sealing around the outer surface of the tube 262 so that the exhaust gas may flow into and through the openings 266, through the channel 268, and out through tubing 172. The flexibility of the tube 262 may also allow for the support member 260 to bend and flex further allowing for tenting of the bag material and the maintenance of the channels 198 around the support member 260.

Figure 16A:
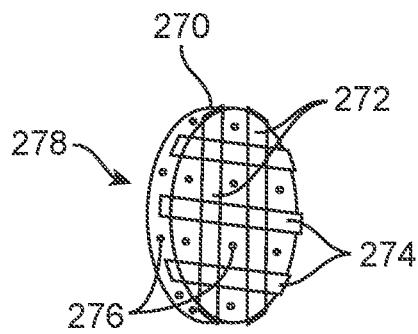
FIGS. 16A and 16B show perspective and side views of yet another variation of a support member having first set of projections and a second set of projections over the surface of the support member.
Figure 16B:
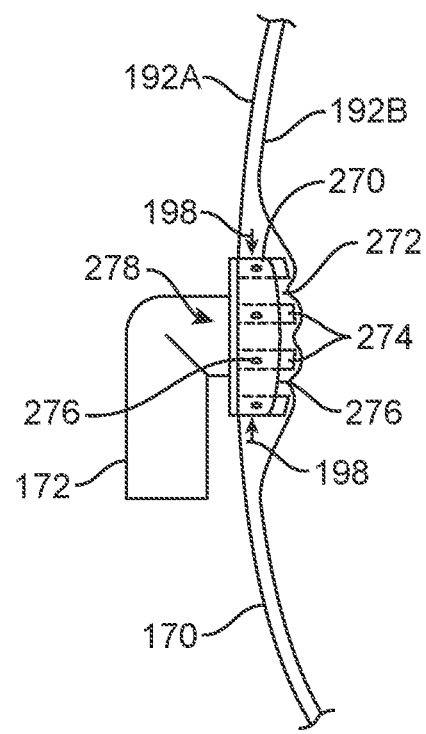

FIG. 16A shows a perspective view of yet another variation of a support member 270 having first set of projections 272 formed to extend parallel to one another in a first direction over the surface of the support member 270 and a second set of projections 274 formed to extend parallel to one another in a second direction over the surface of the support member 270 and extending at an angle (or transverse) relative to the first set of projections 272. The resulting construct may form a waffled or uneven surface to help maintain clearance of the layer 192B. One or more openings 276 may be defined through the support member in fluid communication with the channel 278. FIG. 16B shows a side view illustrating how the support member 270 may maintain clearance of the openings 276 due to the uneven surface presented to the layer 192B to help clear the exhaust gas.

Figure 17A:
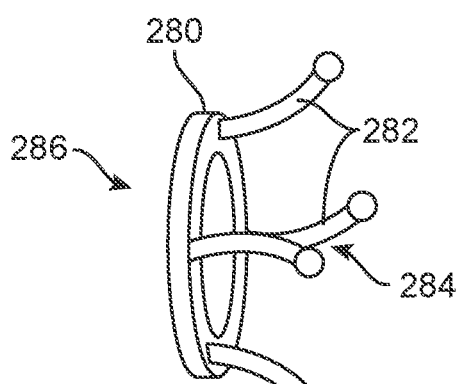
FIGS. 17A and 17B show perspective and side views of yet another variation in which the support member may have one or more projections with atraumatic ends forming a clearance channel between each of the projections.
Figure 17B:
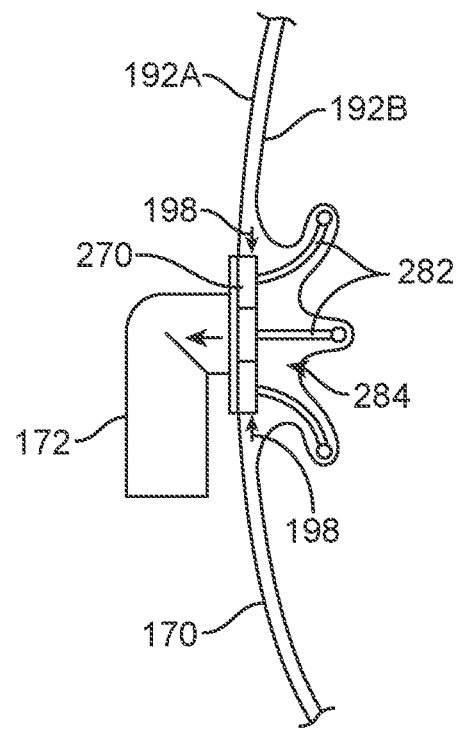

FIG. 17A shows a perspective view of yet another variation in which the support member 280 may have one or more projections 282 with atraumatic ends forming a clearance channel 284 between each of the projections 282. FIG. 17B shows a side view illustrating how the projections 282 may tent the layer 192B to maintain the clearance channel 284 to allow for the exhaust gas to flow through the channel 286 and out of the tubing 172. The number of projections 282 and spacing between may be varied depending upon the amount of clearance to be maintained.

Figure 18C:
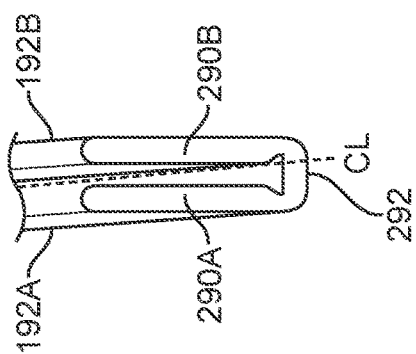
FIGS. 18A to 18C show detail side views of yet another variation of an internal support mechanism configured to maintain the bag in an expanded configuration to prevent the layers from collapsing upon one another.
Figure 18B:
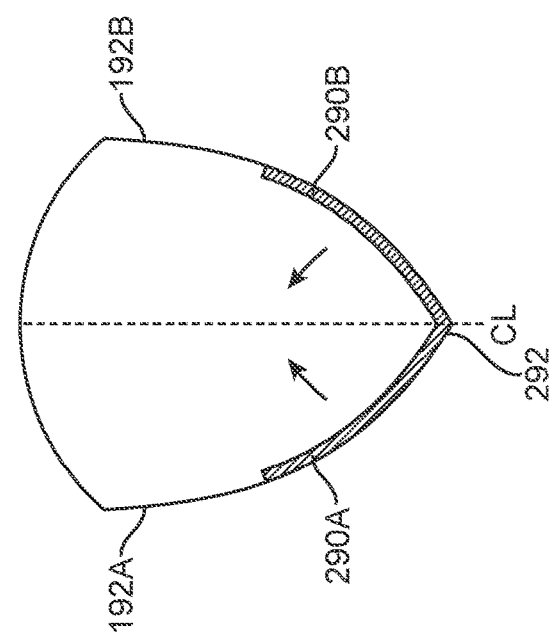
Figure 18A:
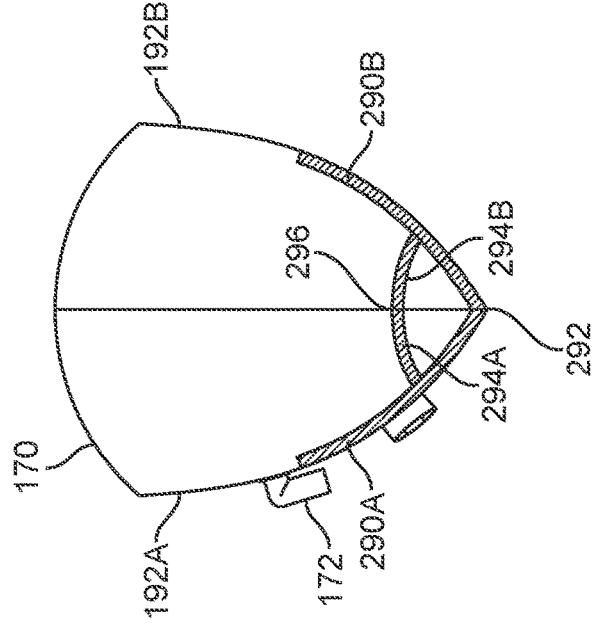
Figure 19C:
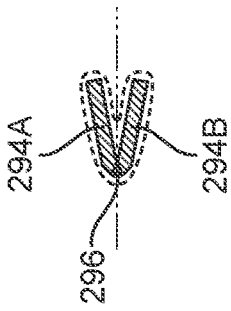
FIGS. 19A to 19C show top views of the bag correlating to FIGS. 18A to 18C.
Figure 19B:
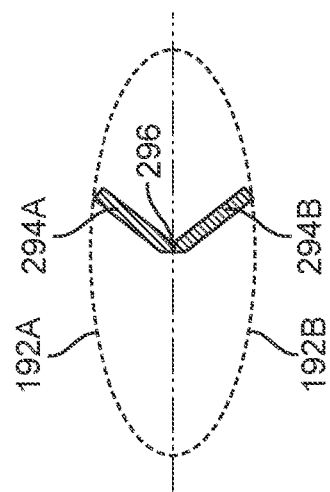
Figure 19A:
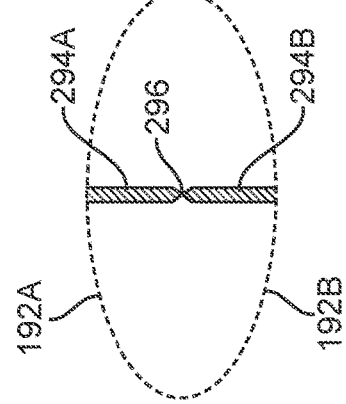

FIGS. 18A to 18C show detail side views of yet another variation of an internal support mechanism configured to maintain the bag 170 in an expanded configuration to prevent the layers 192A, 192B from collapsing upon one another. The support mechanism may be comprised in this variation of a first member 290A and apposed second member 290B connected to one another via a hinged, pivoting, or otherwise collapsible connector 292. An additional scaffold member formed of a first scaffold 294A and apposed second scaffold 294B connected to another via connector 296 may extend between the first and second members 290A, 290B. Once the bag 170 has been evacuated, the expanded bag may be collapsed, e.g., for storage or disposal, by urging the first and second members 290A, 290B towards one another via connector 292, as shown in FIGS. 18B and 18C. The first and second scaffold 294A, 294B are omitted from the figures for clarity but are shown in the top views of FIGS. 19A to 19C which correlate to the collapse of FIGS. 18A to 18C. Similarly, the first and second scaffold 294A, 294B may be collapsed towards one another via the hinge or pivot 296 so that the bag may be reconfigured from its expanded configuration into its fully (or partially) collapsed configuration, as shown.

In yet another variation, FIGS. 20A to 20C show side views of a bag 170 incorporating a self-coiling support member 300 which may extend along the length of the bag 170. The support member 300 may form a structural spine formed integrally along, e.g., second layer 192B of the bag 170, or attached separately to either the bag interior or exterior or between layers of the bag 170 (if formed via multiple layers). The support member 300 may be formed of a coiling structure (e.g., plastics, metals, alloys, etc.) which imparts a collapsing force upon the bag 170. When inflated with the exhaust gas, as shown in FIG. 20A, the bag 170 may maintain is expanded configuration but as the gas is removed from the bag, a first portion 302 of the support member 300 may begin to collapse by coiling. As the first portion 302 of member 300 begins to coil, the first (or upper) portion 304 of the bag 170 may be urged to collapse further forcing any exhaust gas into the second (or lower) portion 306 of the bag 170, as shown in FIG. 20B. As additional exhaust gas is removed from the bag 170, the first portion 302 of support member 300 may fully coil or collapse thereby accelerating the venting of the gas also from the second portion 304 of the bag 170, as shown in FIG. 20C.

This collapsing support member described herein may be used in any number of combinations with any of the other support members described or with any of the other features described herein.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. An exhaust collection apparatus, comprising:
    a first layer and a second layer attached along a periphery and forming an enclosed volume, wherein the periphery defines radiused corners and an extension member which projects from the periphery and forms an attachment point for suspending the exhaust collection apparatus;
    a tubing connector positioned along the first layer and extending through the first layer in fluid communication with the enclosed volume, wherein the tubing connector is located along a centerline of the first layer and near or at a bottom edge of the first layer;
    a support member extending within the enclosed volume and having a contact surface which has a dome-shaped structure and is fluidly coupled to the tubing connector through one or more openings which are defined around a periphery of the support member and away from the contact surface; and
    a drain closure positioned along the first layer and extending through the first layer in fluid communication with the enclosed volume, wherein the drain closure is located away from the centerline and in proximity to the bottom edge.

2. The apparatus of claim 1 wherein the first and second layers are comprised of a lubricious polyurethane having a thickness of 0.003 inches.

3. The apparatus of claim 1 wherein the extension defines an opening therethrough which is reinforced to support 2 lbs for at least 1 hour.

4. The apparatus of claim 1 wherein the first and second layers are configured to elongate up to 800%.

5. The apparatus of claim 1 wherein the apparatus has a burst pressure of at least greater than or equal to 3 psi.

6. The apparatus of claim 1 wherein the first and second layers are transparent.

7. The apparatus of claim 1 wherein the radiused corners have a radius of 11.0 inches.

8. The apparatus of claim 1 wherein the radiused corners comprises four radiused corners.

9. The apparatus of claim 1 wherein the one or more openings are in fluid communication with a channel defined in the support member and with the tubing connector.

10. The apparatus of claim 9 wherein the support member further defines an opening along the contact surface.

11. The apparatus of claim 1 wherein the support member has a curved interface member.

12. The apparatus of claim 1 further comprising an internal support mechanism configured to prevent the first and second layers from collapsing upon one another.

13. The apparatus of claim 1 further comprising a self-coiling support member extending along a length of the exhaust collection apparatus.

14. An exhaust collection apparatus, comprising:
    a first layer and a second layer attached along a periphery and forming an enclosed volume, wherein the periphery defines radiused corners and an extension member which projects from the periphery and forms an attachment point for suspending the exhaust collection apparatus;
    a tubing connector positioned along the first layer and extending through the first layer in fluid communication with the enclosed volume, wherein the tubing connector is located near or at a bottom edge of the first layer;
    a drain closure positioned along the first layer and extending through the first layer in fluid communication with the enclosed volume, wherein the drain closure is located away from the centerline and in proximity to the bottom edge; and
    a support member fluidly coupled to the tubing connector and extending within an interior of the enclosed volume, wherein the support member has a contact surface which has a dome-shaped structure and which is configured to inhibit the first layer and second layer from adhering to one another, wherein the support member is fluid coupled to the tubing connector through one or more openings which are defined around a periphery of the support member and away from the contact surface.

15. The apparatus of claim 14 wherein the first and second layers are comprised of a lubricious polyurethane having a thickness of 0.003 inches.

16. The apparatus of claim 14 wherein the first and second layers are configured to elongate up to 800%.

17. The apparatus of claim 14 wherein the apparatus has a burst pressure of at least greater than or equal to 3 psi.

18. The apparatus of claim 14 wherein the first and second layers are transparent.

19. The apparatus of claim 14 wherein the radiused corners have a radius of 11.0 inches.

20. The apparatus of claim 14 wherein the extension defines an opening there through which is reinforced to support 2 lbs for at least 1 hour.

21. The apparatus of claim 14 wherein the tubing connector is located along a centerline of the first layer.

22. The apparatus of claim 14 wherein the one or more openings are in fluid communication with a channel defined in the support member and with the tubing connector.

23. The apparatus of claim 14 wherein the support member further defines an opening along the contact surface.

24. The apparatus of claim 14 wherein the support member has a curved interface member.

25. The apparatus of claim 14 further comprising a self-coiling support member extending along a length of the exhaust collection apparatus.

* * * * *